(12) United States Patent
O'Hagan et al.

(10) Patent No.: US 7,731,967 B2
(45) Date of Patent: Jun. 8, 2010

(54) COMPOSITIONS FOR INDUCING IMMUNE RESPONSES

(75) Inventors: Derek O'Hagan, Berkeley, CA (US); Manmohan Singh, San Ramon, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 10/837,117

(22) Filed: Apr. 29, 2004

(65) Prior Publication Data

US 2005/0107322 A1 May 19, 2005

Related U.S. Application Data

(60) Provisional application No. 60/466,948, filed on Apr. 30, 2003.

(51) Int. Cl.
 *A61K 39/00* (2006.01)
(52) U.S. Cl. .............. 424/184.1; 424/201.1; 424/202.1; 424/203.1; 424/204.1; 424/278.1
(58) Field of Classification Search ............... 435/4, 435/5, 6, 278.1; 424/70.11, 70.19, 204.1
 See application file for complete search history.

(56) References Cited

U.S. PATENT DOCUMENTS

| 5,389,640 A | | 2/1995 | Gerster et al. |
| 6,146,632 A | * | 11/2000 | Momin et al. ............ 424/184.1 |
| 2003/0139364 A1 | | 7/2003 | Krieg et al. |

FOREIGN PATENT DOCUMENTS

| EP | 0142193 A1 * | 5/1985 |
| WO | WO 98/33487 | 8/1998 |
| WO | WO 98/50071 | 11/1998 |
| WO | WO 00/06123 | 2/2000 |
| WO | 01/26681 | 4/2001 |
| WO | WO 02/24225 A1 | 3/2002 |
| WO | WO 03/028656 A2 | 4/2003 |
| WO | WO 03/028661 A2 | 4/2003 |
| WO | WO 03/070909 A2 | 8/2003 |
| WO | WO 03/077944 A1 | 9/2003 |
| WO | WO 03/080114 A2 | 10/2003 |
| WO | WO 03/094836 A2 | 11/2003 |

OTHER PUBLICATIONS

Menyhart, Lisa, Lyophilization: Freeze-Drying A Downstream Process, Dec. 6, 1995, three pages; available from http://www.rpi.edu/dept/chem-eng/Biotech-Environ/LYO/.*

Wang et al., International Journal of Pharmaceutics, 1998, 166:1-14.*

Imbertson et al., "Antiviral and Immunomodulating Activities of the Imidazoquinoline S-28463", Antiviral Research 26:A301, Mar. 1995.

St. Clair, N. et al., "Cross-Linked Protein Crystals for Vaccine Delivery", Applied Biol. Sci., 96:9469-9474, 1999.

K. F. Griffin, et al., "Immune Responses to V Antigen of *Yersinia pestis* Co-Encapsulated with IFN-γ: Effect of Dose and Formulation", *Vaccine*, vol. 16, No. 5, Mar. 1998, pp. 517-521.

U. R. Hengge, et al., "Tropical Immunomodulators-Progress Towards Treating Inflammation, Infection, and Cancer", *Lancet Infectious Diseases*, vol. 1, No. 3, Oct. 2001, pp. 189-198.

Francesca Brugnolo, et al., "The Novel Synthetic Immune Response Modifier R-848 (Resiquimod) Shifts Human Allergen-Specific CD4+ $T_H2$ Lymphocytes Into IFN-γ-Producing Cells", *Journal of Allergy and Clinical Immunology*, vol. 111, No. 2, Feb. 2003, pp. 380-388.

D.H. Dockrell, et al., "Imiquimod and Resiquimod As Novel Immunomodulators", *Journal of Antimicrobial Chemotherapy*, vol. 48, No. 6, Dec. 2001, pp. 751-755.

K.D. Newman, et al., "Ovalbumin Peptide Encapsulated in Poly(*d,l* lactic-co-glycolic acid) Microspheres is Capable of Inducing a T Helper Type 1 Immune Response", *Journal of Controlled Release*, vol. 54, No. 1, Jun. 1998, pp. 49-59.

P. Johansen, et al. "Revisiting PLA/PLGA Microspheres: An Analysis of Their Potential in Parenteral Vaccination", *European Journal of Pharmaceutics and Biopharmaceutics*, vol. 50, No. 1, Jul. 3, 2000, pp. 129-146.

A. Spickler et al., "Adjuvants in Veterinary Vaccines: Modes of Action and Adverse Effects", J Vet Intern Med 2003;17:273-281.

(Continued)

*Primary Examiner*—Stacy B Chen
(74) *Attorney, Agent, or Firm*—Helen Lee; David Bonham; Robert Gorman

(57) ABSTRACT

The invention provides, inter alia, immunogenic compositions comprising a first antigen, at least two adjuvants, wherein a first adjuvant comprises a polymer derived from poly(lactides) and/or poly(lactide-co-glycolides), and wherein a second adjuvant comprises an imidazoquinoline, wherein said first antigen is encapsulated within, adsorbed or conjugated to, co-lyophilized or mixed with said first adjuvant, and a pharmaceutically acceptable excipient, wherein said composition elicits a cellular immune response when administered to a vertebrate subject. The invention also provides methods of producing immunogenic compositions, methods for producing a cytotoxic-T lymphocyte (CTL) response in a vertebrate subject, and methods of immunization.

89 Claims, 3 Drawing Sheets

OTHER PUBLICATIONS

J. Cox et al., "Adjuvants—A Classification and Review of Their Modes of Action", Vaccine, vol. 15, No. 3, pp. 248-256, 1997.

N. Burdin et al., "Immunological Foundations to the Quest of New Vaccine Adjuvants", Biodrugs 2004; 18 (2): 79-93.

Kensil et al., "Current vaccine adjuvants: an overview of a diverse class," *Frontiers in Bioscience* (2004) 9:2972-2988.

Vasilakos et al., "Adjuvant activities of immune response modifier R-848: comparison with CpG ODN," *Cellular Immunology* (2000) 204:64-74.

\* cited by examiner

COMPOSITIONS FOR INDUCING IMMUNE RESPONSES

CROSS REFERENCE TO RELATED APPLICATIONS

The present application claims priority benefit of U.S. Provisional Application 60/466,948, filed Apr. 30, 2003, which is hereby incorporated by reference in its entirety.

FIELD OF THE INVENTION

The present invention relates generally to immunogenic agents and to agents which enhance the immune response to a selected antigen. In particular, the invention pertains to immunogenic compositions comprising a first antigen, at least two adjuvants, wherein a first adjuvant comprises a polymer derived from poly(lactides) and/or poly(lactide-co-glycolides), and wherein a second adjuvant comprises an imidazoquinoline, wherein said first antigen is encapsulated within, adsorbed or conjugated to, co-lyophilized or mixed with said first adjuvant, and a pharmaceutically acceptable excipient. When administered to a vertebrate subject the composition elicits a cellular immune response.

BACKGROUND OF THE INVENTION

Numerous vaccine formulations have been developed which include attenuated pathogens or subunit protein antigens. Conventional vaccine compositions often include immunological adjuvants to enhance cell-mediated and humoral immune responses. For example, depot adjuvants are frequently used which adsorb and/or precipitate administered antigens and which can retain the antigen at the injection site. Typical depot adjuvants include aluminum compounds and water-in-oil emulsions. However, depot adjuvants, although increasing antigenicity, often provoke severe persistent local reactions, such as granulomas, abscesses and scarring, when injected subcutaneously or intramuscularly. Other adjuvants, such as lipopolysacharrides, can elicit pyrogenic responses upon injection and/or Reiter's symptoms (influenza-like symptoms, generalized joint discomfort and sometimes anterior uveitis, arthritis and urethritis). Saponins, such as *Quillaja saponaria*, have also been used as immunological adjuvants in vaccine compositions against a variety of diseases.

Complete Freund's adjuvant (CFA) is a powerful immunostimulatory agent that has been successfully used with many antigens oh an experimental basis. CFA includes three components: a mineral oil, an emulsifying agent, and killed mycobacteria, such as *Mycobacterium tuberculosis*. Although effective as an adjuvant, CFA causes severe side effects primarily due to the presence of the mycobacterial component, including pain, abscess formation and fever. CFA, therefore, is not used in human and veterinary vaccines.

Incomplete Freund's adjuvant (IFA) is similar to CFA but does not include the bacterial component. IFA, while not approved for use in the United States, has been used elsewhere in human vaccines for influenza and polio and in veterinary vaccines for rabies, canine distemper and foot-and-mouth disease. However, evidence indicates that both the oil and emulsifier used in IFA can cause tumors in mice.

Despite the presence of such adjuvants, conventional vaccines often fail to provide adequate protection against the targeted pathogen. In this regard, there is growing evidence that vaccination against intracellular pathogens, such as a number of viruses, should target both the cellular and humoral arms of the immune system. More particularly, cytotoxic T-lymphocytes (CTLs) play an important role in cell-mediated immune defense against intracellular pathogens such as viruses and tumor-specific antigens produced by malignant cells. CTLs mediate cytotoxicity of virally infected cells by recognizing viral determinants in conjunction with class I major histocompatibility complex (MHC) molecules displayed by the infected cells. Cytoplasmic expression of proteins is a prerequisite for class I MHC processing and presentation of antigenic peptides to CTLs. However, immunization with killed or attenuated viruses often fails to produce the CTLs necessary to curb intracellular infection. Furthermore, conventional vaccination techniques against viruses displaying marked genetic heterogeneity and/or rapid mutation rates that facilitate selection of immune escape variants, such as HIV or influenza, are problematic. Accordingly, alternative techniques for vaccination have been developed.

Particulate carriers with adsorbed or entrapped antigens have been used in an attempt to circumvent these problems and in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as polymer particles derived from poly(lactides) and poly(lactide-co-glycolides), known as PLG. While offering significant advantages over other more toxic systems, antigen-containing PLG particles to-date suffer from some drawbacks. For example, large-scale production and manufacturing of particulate carriers may be problematic due to the high cost of the polymers used in the manufacture the particulate carriers.

Liposomes have also been employed in an effort to overcome these problems. Liposomes are microscopic vesicles formed from lipid constituents such as phospholipids which are used to entrap pharmaceutical agents. Although the use of liposomes as a drug delivery system alleviates some of the problems described above, liposomes exhibit poor stability during storage and use, and large-scale production and manufacturing of liposomes is problematic.

International Publication No. WO 98/50071 describes the use of viral-like particles (VLPs) as adjuvants to enhance immune responses of antigens administered with the VLPs. St. Clair et al. describe the use of protein crystals to enhance humoral and cellular responses. (St. Clair, N. et al., Applied Biol. Sci., 96:9469-9474, 1999).

Despite the above-described adjuvant and antigen-presentation systems, there is a continued need for effective, safe and cost-efficient compositions with improved purity, stability and immunogenicity.

SUMMARY OF THE INVENTION

The inventors herein have found, surprisingly, that immunogenic compositions comprising a first antigen, at least two adjuvants, wherein a first adjuvant comprises a polymer derived from poly(lactides) and/or poly(lactide-co-glycolides), and wherein a second adjuvant comprises an imidazoquinoline, wherein said first antigen is encapsulated within, adsorbed or conjugated to, co-lyophilized or mixed with said first adjuvant, and a pharmaceutically acceptable excipient, have an inhibitory effect on induction of antigen (Ag)-specific IFNγ-secreting cells, while having no inhibitory or stimulatory effect on the induction of antigen-specific IL4- secreting cells. The present invention is directed in some embodiments to the use of such compositions.

The present invention provides immunogenic compositions comprising a first antigen, at least two adjuvants, wherein a first adjuvant comprises a polymer derived from poly(lactides) and/or poly(lactide-co-glycolides), and wherein a second adjuvant comprises an imidazoquinoline, wherein said first antigen is encapsulated within, adsorbed or conjugated to, co-lyophilized or mixed with said first adjuvant, and a pharmaceutically acceptable excipient, wherein said composition elicits a cellular immune response when administered to a vertebrate subject. In some embodiments the composition comprises an imidazoquinoline.

In some embodiments, the present invention provides immunogenic compositions comprising a first antigen, at least two adjuvants, wherein a first adjuvant comprises a polymer derived from poly(lactides) and/or poly(lactide-co-glycolides), wherein a second adjuvant comprises an imidazoquinoline, and a pharmaceutically acceptable excipient, wherein the first antigen is a particle produced by a process comprising the steps of: (a) adding a precipitation agent to an aqueous solution of an antigen and stirring the resulting mixture to form the particle; (b) stabilizing the antigen particle by a stabilizing treatment; and (c) recovering the antigen particle from the aqueous solution.

In some embodiments, the present invention provides methods for eliciting a cytotoxic-T lymphocyte (CTL) response in a vertebrate subject comprising administering to the vertebrate subject an immunogenic composition of the present invention.

In some embodiments, the present invention provides methods of eliciting an immune response in a vertebrate subject comprising administering to the vertebrate subject an effective amount of the immunogenic composition.

The present invention also provides injectable vaccine compositions comprising immunogenic compositions of the present invention.

In some embodiments, the present invention provides methods of eliciting an antibody-mediated immune response in an individual comprising administering an immunogenic composition of the present invention to the individual.

In some embodiments, the present invention provides methods of making the immunogenic compositions comprising: (a) combining a precipitation agent with an aqueous solution comprising an antigen; (b) dispersing the resultant mixture to form antigen particles; (c) stabilizing the dispersed antigen particles by a stabilizing treatment; (d) recovering the stabilized antigen particle; and (e) combining the stabilized antigen particle with a pharmaceutically acceptable excipient.

In some embodiments, the present invention provides stabilized particles capable of eliciting a cytotoxic-T lymphocyte (CTL) response, wherein the stabilized particle is a generally spherical particle that is produced by a process comprising: (a) forming a particle from antigen; (b) stabilizing the particle by a stabilizing treatment, wherein the stabilized particle is not a virus-like particle, and wherein the stabilized particle is not entrapped within a carrier; and (c) adding an adjuvant comprising R-848.

In some embodiments, the present invention provides methods of preparing an immunogenic composition comprising combining a stabilized particle with one or more pharmaceutically acceptable excipients.

In some embodiments, the present invention provides pharmaceutical compositions comprising an immunogenic composition of the present invention.

In some embodiments, the present invention provides pharmaceutical compositions comprising a stabilized particle.

In some embodiments, the present invention provides kits for preparing an immunogenic composition comprising a first container comprising an antigen, a second container comprising an imidazoquinoline, and a third container comprising a polymer derived from poly(lactides) and/or poly(lactide-co-glycolides).

These and other embodiments of the present invention will readily occur to those of ordinary skill in the art in view of the disclosure herein.

DETAILED DESCRIPTION OF THE INVENTION

Figure 1:
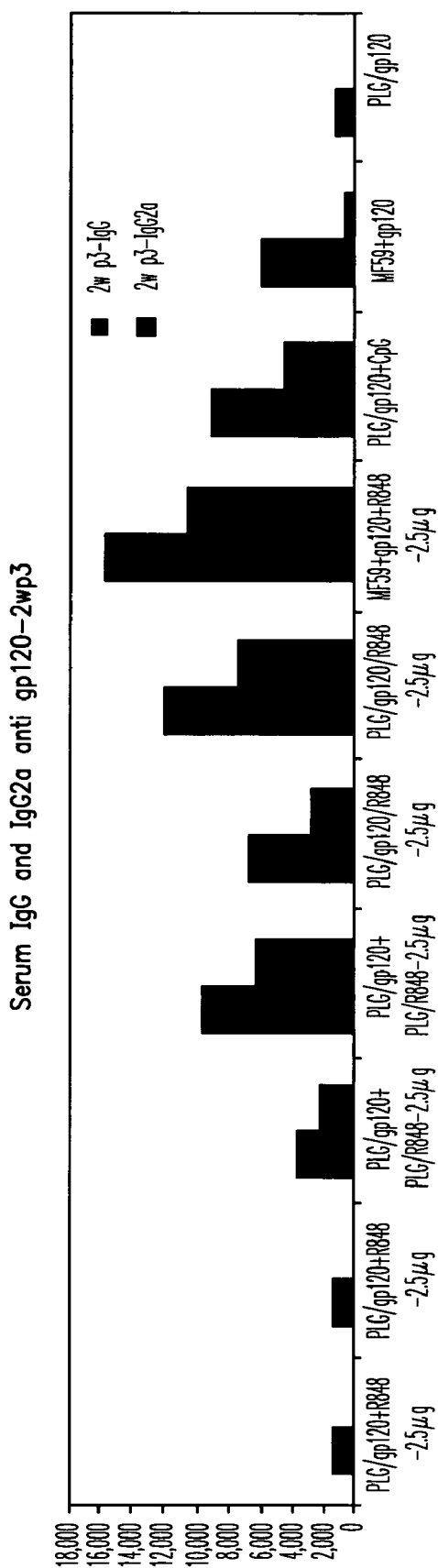
FIG. 1 shows IgG and IgG2a antibody titers from mice immunized with gp120 associated with PLG plus R848 (2.5 µg); gp120 associated with PLG plus R848 (25 µg); gp120 associated with PLG plus R848 (2.5 µg) associated with PLG; gp120 associated with PLG plus R848 (25 µg) associated with PLG; gp120 associated with PLG and with R848 (2.5 µg); gp120 associated with PLG and with R848 (25 µg); gp120 and MF59 and R848 (25 µg); gp120 associated with PLG, plus CpG; gp120 plus MF59; and gp120 associated with PLG. Bars show the geometric mean antibody titer (GMT) of the group of mice. The error bars represent standard error of the mean.

The practice of the present invention will employ, unless otherwise indicated, conventional methods of virology, chemistry, biochemistry, recombinant technology, immunology and pharmacology, within the skill of the art. Such techniques are explained fully in the literature. See, e.g., Virology, 3rd Edition, vol. I & II (B. N. Fields and D. M. Knipe, eds., 1996); Remington's Pharmaceutical Sciences, 18th Edition (Easton, Pa.: Mack Publishing Company, 1990); Methods In Enzymology (S. Colowick and N. Kaplan, eds., Academic Press, Inc.); Handbook of Experimental Immunology, Vols. I-IV (D. M. Weir and C. C. Blackwell, eds., 1986, Blackwell Scientific Publications); Sambrook et al., Molecular Cloning: A Laboratory Manual (2nd Edition, 1989); and DNA Cloning: A Practical Approach, vol. I & II (D. Glover, ed.).

The present invention provides immunogenic compositions comprising a first antigen, at least two adjuvants, wherein a first adjuvant comprises a polymer derived from poly(lactides) and/or poly(lactide-co-glycolides), and wherein a second adjuvant comprises an imidazoquinoline, wherein said first antigen is encapsulated within, adsorbed or conjugated to, co-lyophilized or mixed with said first adjuvant, and a pharmaceutically acceptable excipient, wherein said composition elicits a cellular immune response when administered to a vertebrate subject. In some embodiments the antigen is in the form of a particle produced as described herein or by other means known to those of skill in the art. In some embodiments the antigen is a nucleic acid molecule that is linked to a regulatory sequence which controls expression of the nucleic acid molecule. In some embodiments the composition comprises R-848 formulated with PLG.

The present invention also provides immunogenic composition comprising a first antigen, at least two adjuvants, wherein a first adjuvant comprises a polymer derived from poly(lactides) and/or poly(lactide-co-glycolides), wherein a second adjuvant comprises an imidazoquinoline, and a pharmaceutically acceptable excipient, wherein the first antigen is a particle produced by a process comprising the steps of: (a) adding a precipitation agent to an aqueous solution of an antigen and stirring the resulting mixture to form the particle; (b) stabilizing the antigen particle by a stabilizing treatment; and (c) recovering the antigen particle from the aqueous solution. In some embodiments, step (a) or the process to produce a particle (i.e. an antigen particle) can further include an acid. Examples of acids include, but not limited to, acetic acid, glycolic acid, hydroxybutyric acid, hydrochloric acid or lactic acid. In some embodiments, the process of producing a particle includes a solvent evaporation technique. Solvent evaporation techniques are known to those of skill in the art and described herein. Examples of precipitation agents include, but are not limited to, one or more of oils, hydrocarbons or coacervation agents.

The immunogenic compositions can further comprise at least a third adjuvant or more than 3, 4, or 5 additional adjuvants. In some embodiments, the immunogenic composition comprises R-848, MF59, or combinations thereof.

The stabilizing treatment performed to prepare or make the particles can, for example, comprise one or more of heat treatment or treatment with a chemical cross-linking agent. Processes of heat treatment or chemical-cross linking are described herein and known to one of ordinary skill in the art.

In some embodiments, the compositions further comprise a second antigen. In some embodiments, the second antigen is distinct from the first antigen. The second antigen is a nucleic acid molecule, protein, or peptide.

In some embodiments, the particles described herein can be generally spherical. In some embodiments, the particles or stabilized particles have a diameter from about 200 nanometers to about 10 microns or from about 500 nanometers to about 5 microns.

Immunogenic compositions can also be used in methods for eliciting a cytotoxic-T lymphocyte (CTL) response, antibody-mediated immune response, or an immune response in a vertebrate subject comprising administering to the vertebrate subject the immunogenic composition.

In some embodiments, the immunogenic compositions are used in an injectable vaccine to provide protection against a antigen, pathogen or protein.

In some embodiments the present invention provides immunogenic compositions comprising a first antigen, one or more adjuvants wherein at least one of said adjuvants comprises a polymer derived from poly(lactides) and/or poly(lactide-co-glycolides), and a pharmaceutically acceptable excipient, wherein at least one adjuvant is encapsulated within, adsorbed or conjugated to, co-lyophilized or mixed with said first antigen, and wherein said composition elicits a cellular immune response when administered to a vertebrate subject.

The present invention also provides methods of making immunogenic compositions, the methods comprising (a) combining a precipitation agent with an aqueous solution comprising an antigen; (b) dispersing the resultant mixture to form antigen particles; (c) stabilizing the dispersed antigen particles by a stabilizing treatment; (d) recovering the stabilized antigen particle; and (e) combining the stabilized antigen particle with a pharmaceutically acceptable excipient. In some embodiments, the production of antigen particles further comprises a solvent evaporation technique. In some embodiments the composition comprises R-848 formulated with PLG.

Stabilized particles capable of eliciting a cytotoxic-T lymphocyte (CTL) response, wherein the stabilized particle is a generally spherical particle, can be produced by a process comprising: (a) forming a particle from antigen; (b) stabilizing the particle by a stabilizing treatment, wherein the stabilized particle is not a virus-like particle, and wherein the stabilized particle is not entrapped within a carrier; and (c) adding an adjuvant comprising R-848.

Immunogenic compositions can also be prepared as pharmaceutical compositions.

In some embodiments, the immunogenic compositions comprise conventional adjuvants.

The present invention also provides kits for preparing an immunogenic composition. The kits comprise a first container comprising an antigen and a second container comprising a polymer derived from poly(lactides) and/or poly(lactide-co-glycolides). In some embodiments, the kits further comprise a third container comprising R-848.

As used herein, the singular forms "a," "an" and "the" include plural references unless the content clearly dictates otherwise.

As used herein, the term "about" refers to +/−10% of a value.

The term "R-848" refers to a compound with the chemical name 1H-Imidazo(4,5-c)quinoline-1-ethanol(ethoxymethyl)-Alpha, Alpha-dimethyl and a chemical formula of $C_{17}H_{22}N_4O_2$. R-848 can also be referred to as "resiquimod," "S-28463," and "VML-600." The synthesis of R-848 is described in U.S. Pat. No. 5,389,640, herein incorporated by reference. R-848 is in a class of compounds referred to as imidazoquinolines which have cytokine induction activity. The antiviral and immunomodulating activities of R-848 has been discussed in Imbertson et al. (*Antiviral Research* 26:A301, March 1995).

As used herein, the term "in combination with" is meant to refer to the use of the compositions of the present invention with other therapeutic regimens. In some embodiments, immunogenic compositions of the present invention are used in combination with traditional treatment regimens for diseases or disorders being treated. Administration of the compositions of the present invention may take place prior to, simultaneously with, or after traditional treatments.

As used herein the term "isolated" refers to a polynucleotide, a polypeptide, an antibody, or a host cell that is in an environment different from that in which the polynucleotide, the polypeptide, or the antibody naturally occurs. Methods of isolating cells are well known to those skilled in the art. A polynucleotide, a polypeptide, or an antibody which is isolated is generally substantially purified.

A "purified" protein is a protein which is recombinantly or synthetically produced, or isolated from its natural host, such that the amount of protein present in a composition is substantially higher than that present in a crude preparation. In general, a purified protein will be at least about 50% homogeneous, more preferably at least about 80%, about 85%, about 90%, about 95%, about 97%, about 98%, about 99%, and about 100% homogeneous.

An "immunological response" to an antigen or composition is the development in a subject of a humoral and/or a cellular immune response to the antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the MHC and expressed on the surfaces of cells. CTLs help induce and promote the intracellular destruction of intracellular microbes, or the lysis of cells infected with such microbes. Another aspect of cellular immunity involves an antigen-specific response by helper T-cells which act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

For purposes of the present invention, an "effective amount" of an antigen will be that amount which elicits an immunological response when administered, or enhances an immunological response to a coadministered antigen.

As used herein, the phrase "injectable composition", or variants thereof, refers to compositions which satisfy the USP requirements for "injectables", i.e., sterile, pyrogen- and particulate free, and possessing specific pH and isotonicity values.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual along with the antigen formulation without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

An "antigen" refers to a molecule containing one or more epitopes (either linear, conformational or both) that elicit an immunological response, as defined below. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. The term "antigen" denotes both subunit antigens, i.e., antigens which are separate and discrete from a whole organism with which the antigen is associated in nature, as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

As used herein, the term "protein particle" refers to a particle made from a protein.

As used herein, the term "nucleic acid particle" refers to a particle made from a nucleic acid molecule.

For purposes of the present invention, antigens can be derived from any of several known viruses, bacteria, parasites and fungi, as described in further detail below. The term also intends any of the various tumor antigens. For example, antigens may be proteins from or derived from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV such as, including members of the various genetic subtypes of HIV isolates $HIV_{IIIb}$, $HIV_{SF2}$, $HIV_{LAV}$, $HIV_{LAI}$, $HIV_{MN}$, $HIV-1_{CM235}$, $HIV-1_{US4}$, HIV-2; proteins derived from simian immunodeficiency virus (SIV); proteins derived from *Neisseria meningitidis* (A, B, C, Y), *Hemophilus influenza* type B (HIB), *Helicobacter pylori*; human serum albumin and ovalbumin. As discussed above, antigens may also be nucleic acids which express an antigen or antigenic determinant in vivo.

As used herein, the term "PLG" refers to poly(lactide-coglycolides), (see International Publications WO 00/06123 and WO 98/33487, each of which is incorporated by reference in its entirety).

As used herein, "coacervation" refers to the phase separation of a liquid polymer-rich phase from a macromolecular solution when the solubility is reduced by some chemical or physical means. The drug to be encapsulated is dispersed in a solution of a macromolecule in which it is immiscible. A non-solvent, miscible with the continuous phase but a poor solvent for the polymer under certain conditions will induce the polymer to form a coacervate layer around the disperse phase. This coating layer may then be treated to give a rigid coat. Examples of coacervation agents include, without limitation, acetone, ethanol, isopropanol, and the like.

As used herein the term "protein" refers to peptides, polypeptides, metalloproteins, glycoproteins and lipoproteins. "Proteins" refer to polymers of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to the native sequence, so long as the protein is capable of acting as an antigen and eliciting a CTL response.

Preferred substitutions are those which are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity of the protein, are therefore within the definition of the reference polypeptide.

The term "fragment" as used herein refers to a physically contiguous portion of the primary structure of a biomolecule. In the case of proteins, a fragment is defined by a contiguous portion of the amino acid sequence of that protein and refers to at least 3-5 amino acids, at least 8-10 amino acids, at least 11-15 amino acids, at least 17-24 amino acids, at least 25-30 amino acids, and at least 30-45 amino acids. In the case of polynucleotides, a fragment is defined by a contiguous portion of the nucleic acid sequence of that polynucleotide and refers to at least 9-15 nucleotides, at least 18-30 nucleotides, at least 33-45 nucleotides, at least 48-72 nucleotides, at least 75-90 nucleotides, and at least 90-130 nucleotides. In some embodiments, fragments of biomolecules are immunogenic fragments.

In some embodiments, the antigen is a protein particle. Protein particles may have the following physical characteristics. The protein particles are generally spherical in shape and possess a diameter of about 150 nm to about 10 μm, about 200 nm to about 4 μm, and preferably about 250 nm to about 3 μm in diameter. Generally, the protein particles are obtained by denaturing and cross-linking the protein, followed by stabilization of the cross-linked protein.

Examples of antigens useful in the present invention are set forth, for example, in U.S. patent application Ser. No. 10/265,083, filed Oct. 3, 2002, which is hereby incorporated by reference in its entirety.

Antigens useful in the present invention include for example and without limitation, nucleic acids expressing proteins or proteins derived from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., Cytomegaloviruses (J. K. McDougall, ed., Springer-Verlag 1990) pp. 125-169, for a review of the protein coding content of cytomegalovirus; McGeoch et al., J. Gen. Virol. (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., Nature (1984) 310:207-211, for the identification of protein coding sequences in an EBV genome; and Davison and Scott, J. Gen. Virol. (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436, incorporated by reference herein in their entireties. The HCV genome encodes several viral proteins, discussed further below. These proteins, as well as antigenic fragments thereof, will find use in the present methods. Similarly, the sequence for the .delta.-antigen from HDV is known (see, e.g., U.S. Pat. No. 5,378,814) and this sequence can also be conveniently used in the present methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines— from the laboratory to license: a case study" in Mackett, M. and Williamson, J. D., Human Vaccines and Vaccination, pp. 159-176, for a discussion of HBV structure; and U.S. Pat. Nos. 4,722,840, 5,098,704, 5,324,513, incorporated herein by reference in their entireties; Beames et al., J. Virol. (1995) 69:6833-6838, Birnbaum et al., J. Virol. (1990) 64:3319-3330; and Zhou et al., J. Virol. (1991) 65:5457-5464.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses.

More particularly, the gp120 envelope protein from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., Human Retroviruses and Aids, 1990, Los Alamos, N. Mex.: Los Alamos National Laboratory; and Modrow et al., J. Virol. (1987) 61:570-578, for a comparison of the envelope gene sequences of a variety of HIV isolates) and sequences derived from any of these isolates will find use in the present methods. Furthermore, the invention is equally applicable to other immunogenic proteins derived from any of the various HIV isolates, including any of the various envelope proteins such as gp160, gp140 and gp41, gag antigens such as p24gag and p55gag, as well as proteins derived from the pol region.

Influenza virus is another example of a virus for which the present invention is useful. Specifically, the envelope glycoproteins HA and NA of influenza A are of particular interest for generating an immune response. Numerous HA subtypes of influenza A have been identified (Kawaoka et al., Virology (1990) 179:759-767; Webster et al., "Antigenic variation among type A influenza viruses," p. 127-168. In: P. Palese and D. W. Kingsbury (ed.), Genetics of influenza viruses. Springer-Verlag, New York). Thus, proteins derived from any of these isolates can also be used in the invention described herein.

Antigens for use in the compositions and methods described herein may also be derived from numerous bacterial antigens, such as those from organisms that cause diphtheria, cholera, tuberculosis, tetanus, pertussis, meningitis, and other pathogenic states, including, without limitation, *Meningococcus* A, B and C, *Hemophilus influenza* type B (HIB), and *Helicobacter pylori*. Examples of parasitic antigens include those derived from organisms causing malaria and Lyme disease.

Furthermore, the compositions and methods described herein provide a means for treating a variety of malignant cancers. For example, the system of the present invention can be used to mount both humoral and cell-mediated immune responses to particular proteins specific to the cancer in question, such as an activated oncogene, a fetal antigen, or an activation marker. Such tumor antigens include any of the various MAGEs (melanoma associated antigen E), including MAGE 1, 2, 3, 4, etc. (Boon, T. Scientific American (March 1993):82-89); any of the various tyrosinases; MART 1 (melanoma antigen recognized by T cells), mutant ras; mutant p53; p97 melanoma antigen; CEA (carcinoembryonic antigen), among others.

It is readily apparent that the present invention can be used to raise antibodies to a large number of antigens for diagnostic and immunopurification purposes, as well as to prevent or treat a wide variety of diseases.

As explained above, the compositions and methods of the present invention may employ HCV antigens. The genome of the hepatitis C virus typically contains a single open reading frame of approximately 9,600 nucleotides, which is transcribed into a polyprotein. The full-length sequence of the polyprotein is disclosed in European Publication No. 388,232 and U.S. Pat. No. 6,150,087, incorporated herein by reference in their entireties. As shown in Table 1, An HCV polyprotein, upon cleavage, produces at least ten distinct products, in the order of $NH_2$-Core-E 1-E2-p7-NS2-NS3-NS4a-NS4b-NS5a-NS5b-COOH. The core polypeptide occurs at positions 1-191, numbered relative to HCV-1 (see, Choo et al. (1991) Proc. Natl. Acad. Sci. USA 88:2451-2455, for the HCV-1 genome). This polypeptide is further processed to produce an HCV polypeptide with approximately amino acids 1-173. The envelope polypeptides, E1 and E2, occur at about positions 192-383 and 384-746, respectively. The P7 domain is found at about positions 747-809. NS2 is an integral membrane protein with proteolytic activity and is found at about positions 810-1026 of the polyprotein. NS2, either alone or in combination with NS3 (found at about positions 1027-1657), cleaves the NS2—NS3 sissle bond which in turn generates the NS3 N-terminus and releases a large polyprotein that includes both serine protease and RNA helicase activities. The NS3 protease, found at about positions 1027-1207, serves to process the remaining polyprotein. The helicase activity is found at about positions 1193-1657. Completion of polyprotein maturation is initiated by autocatalytic cleavage at the NS3—NS4a junction, catalyzed by the NS3 serine protease. Subsequent NS3-mediated cleavages of the HCV polyprotein appear to involve recognition of polyprotein cleavage junctions by an NS3 molecule of another polypeptide. In these reactions, NS3 liberates an NS3 cofactor (NS4a, found about positions 1658-1711), two proteins (NS4b found at about positions 1712-1972, and NS5a found at about positions 1973-2420), and an RNA-dependent RNA polymerase (NS5b found at about positions 2421-3011).

Sequences for HCV polyprotein products, and immunogenic polypeptides derived therefrom, are known (see, e.g., U.S. Pat. No. 5,350,671, incorporated herein by reference in its entirety). For example, a number of general and specific immunogenic polypeptides, derived from the HCV polyprotein, have been described. See, e.g., Houghton et al., European Publ. Nos. 318,216 and 388,232; Choo et al. Science (1989) 244:359-362; Kuo et al. Science (1989) 244:362-364; Houghton et al. Hepatology (1991) 14:381-388; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778. These publications provide an extensive background on HCV generally, as well as on the manufacture and uses of HCV polypeptide immunological reagents. For brevity, therefore, the disclosure of these publications is incorporated herein by reference.

Any desired antigenic HCV polypeptide can be utilized with the present invention, including, for example, the E1 and/or E2 envelope glycoproteins of HCV, as well as E1 E2 complexes, associated either through non-covalent or covalent interactions Such complexes may be made up of immunogenic fragments of E1 and E2 which comprise epitopes. For example, fragments of E1 polypeptides can comprise from about 5 to nearly the full-length of the molecule, such as 6, 10, 25, 50, 75, 100, 125, 150, 175, 185 or more amino acids of an E1 polypeptide, or any integer between the stated numbers. Similarly, fragments of E2 polypeptides can comprise 6, 10, 25, 50, 75, 100, 150, 200, 250, 300, or 350 amino acids of an E2 polypeptide, or any integer between the stated numbers. The E1 and E2 polypeptides may be from the same or different HCV strains. For example, epitopes derived from, e.g., the hypervariable region of E2, such as a region spanning amino acids 384-410 or 390-410, can be included in the E2 polypeptide. A particularly effective E2 epitope to incorporate into the E2 sequence or E1 E2 complexes is one which includes a consensus sequence derived from this region, such as the consensus sequence for amino acids 390-410 of the HCV type I genome. Additional epitopes of E1 and E2 are known and described in, e.g., Chien et al., International Publication No. WO 93/00365, incorporated by reference herein in its entirety.

Moreover, the E1 and E2 polypeptides may lack all or a portion of the membrane spanning domain. The membrane anchor sequence functions to associate the polypeptide to the endoplasmic reticulum. Normally, such polypeptides are capable of secretion into growth medium in which an organism expressing the protein is cultured. However, as described in International Publication No. WO 98/50556, such polypeptides may also be recovered intracellularly. Secretion into growth medium is readily determined using a number of detection techniques, including, e.g., polyacrylamide gel electrophoresis and the like, and immunological techniques such as immunoprecipitation assays as described in, e.g., International Publication No. WO 96/04301, published Feb. 15, 1996. With E1, generally polypeptides terminating with about amino acid position 370 and higher (based on the numbering of HCV1 E1) will be retained by the ER and hence not secreted into growth media. With E2, polypeptides terminating with about amino acid position 731 and higher (also based on the numbering of the HCV1 E2 sequence) will be retained by the ER and not secreted. (See, e.g., International Publication No. WO 96/04301, published Feb. 15, 1996). It should be noted that these amino acid positions are not absolute and may vary to some degree. Thus, the present invention contemplates the use of E1 and E2 polypeptides which retain the transmembrane binding domain, as well as polypeptides which lack all or a portion of the transmembrane binding domain, including E1 polypeptides terminating at about amino acids 369 and lower, and E2 polypeptides, terminating at about amino acids 730 and lower, are intended to be captured by the present invention. Furthermore, the C-terminal truncation can extend beyond the transmembrane spanning domain towards the N-terminus. Thus, for example, E1 truncations occurring at positions lower than, e.g., 360 and E2 truncations occurring at positions lower than, e.g., 715, are also encompassed by the present invention. All that is necessary is that the truncated E1 and E2 polypeptides remain functional for their intended purpose. However, particularly preferred truncated E1 constructs are those that do not extend beyond about amino acid 300. Most preferred are those terminating at position 360. Preferred truncated E2 constructs are those with C-terminal truncations that do not extend beyond amino acid position 715. Particularly preferred E2 truncations are those molecules truncated after any of amino acids 715-730, such as 725. If truncated molecules are used, it is preferable to use E1 and E2 molecules that are both truncated.

E2 exists as multiple species (Spaete et al., Virol. (1992) 188:819-830; Selby et al., J. Virol. (1996) 70:5177-5182; Grakoui et al., J. Virol. (1993) 67:1385-1395; Tomei et al., J. Virol. (1993) 67:4017-4026) and clipping and proteolysis may occur at the N- and C-termini of the E1 and E2 polypeptides. Thus, an E2 polypeptide for use herein may comprise at least amino acids 405-661, e.g., 400, 401, 402 . . . to 661, such as 384-661, 384-715, 384-746, 384-749 or 384-809, or 384 to any C-terminus between 661-809, of an HCV polyprotein, numbered relative to the full-length HCV-1 polyprotein. Similarly, preferable E1 polypeptides for use herein can comprise amino acids 192-326, 192-330, 192-333, 192-360, 192-363, 192-383, or 192 to any C-terminus between 326-383, of an HCV polyprotein.

The E1 and E2 polypeptides and complexes thereof may also be present as asialoglycoproteins. Such asialoglycoproteins are produced by methods known in the art, such as by using cells in which terminal glycosylation is blocked. When these proteins are expressed in such cells and isolated by GNA lectin affinity chromatography, the E1 and E2 proteins aggregate spontaneously. Detailed methods for producing these E1E2 aggregates are described in, e.g., U.S. Pat. No. 6,074,852, incorporated herein by reference in its entirety. For example, E1E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes of the present invention may be expressed as a fusion protein wherein the desired portion of E1 is fused to the desired portion of E2.

Moreover, the E1 E2 complexes may be present as a heterogeneous mixture of molecules, due to clipping and proteolytic cleavage, as described above. Thus, a composition including E1E2 complexes may include multiple species of E1 E2, such as E1E2 terminating at amino acid 746 (E1E2$_{746}$), E1E2 terminating at amino acid 809 (E1E2$_{809}$), or any of the other various E1 and E2 molecules described above, such as E2 molecules with N-terminal truncations of from 1-20 amino acids, such as E2 species beginning at amino acid 387, amino acid 402, amino acid 403, etc.

E1 E2 complexes are readily produced recombinantly, either as fusion proteins or by e.g., co-transfecting host cells with constructs encoding for the E1 and E2 polypeptides of interest. Co-transfection can be accomplished either in trans or cis, i.e., by using separate vectors or by using a single vector which bears both of the E1 and E2 genes. If done using a single vector, both genes can be driven by a single set of control elements or, alternatively, the genes can be present on the vector in individual expression cassettes, driven by individual control elements. Following expression, the E1 and E2 proteins will spontaneously associate. Alternatively, the complexes can be formed by mixing the individual proteins together which have been produced separately, either in purified or semi-purified form, or even by mixing culture media in which host cells expressing the proteins, have been cultured, if the proteins are secreted. Finally, the E1E2 complexes of the present invention may be expressed as a fusion protein wherein the desired portion of E1 is fused to the desired portion of E2.

Methods for producing E1E2 complexes from full-length, truncated E1 and E2 proteins which are secreted into media, as well as intracellularly produced truncated proteins, are known in the art. For example, such complexes may be produced recombinantly, as described in U.S. Pat. No. 6,121,020; Ralston et al., J. Virol. (1993) 67:6753-6761, Grakoui et al., J. Virol. (1993) 67:1385-1395; and Lanford et al., Virology (1993) 197:225-235.

Other HCV polypeptides may also be used in the invention. For example, HCV polypeptides derived from the Core region, such as polypeptides derived from the region found between amino acids 1-191; amino acids 10-53; amino acids 10-45; amino acids 67-88; amino acids 86-100; 81-130; amino acids 121-135; amino acids 120-130; amino acids 121-170; and any of the Core epitopes identified in, e.g., Houghton et al., U.S. Pat. No. 5,350,671; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties, will find use with the subject compositions and methods.

Additionally, polypeptides derived from the nonstructural regions of the virus will also find use herein. The NS3/4a region of the HCV polyprotein has been described and the amino acid sequence and overall structure of the protein are disclosed in Yao et al. Structure (November 1999) 7:1353-1363. See, also, Dasmahapatra et al., U.S. Pat. No. 5,843,752, incorporated herein by reference in its entirety. As explained above, either the native sequence or immunogenic analogs can be used in the subject formulations. Dasmahapatra et al., U.S. Pat. No. 5,843,752 and Zhang et al., U.S. Pat. No. 5,990,276, both describe analogs of NS3/4a and methods of making the same.

Moreover, polypeptides for use in the subject compositions and methods may be derived from the NS3 region of the HCV polyprotein. A number of such polypeptides are known, including, but not limited to polypeptides derived from the c33c and c100 regions, as well as fusion proteins comprising an NS3 epitope, such as c25. These and other NS3 polypeptides are useful in the present compositions and are known in the art and described in, e.g., Houghton et al, U.S. Pat. No. 5,350,671; Chien et al. Proc. Natl. Acad. Sci. USA (1992) 89:10011-10015; Chien et al. J. Gastroent. Hepatol. (1993) 8:S33-39; Chien et al., International Publ. No. WO 93/00365; Chien, D. Y., International Publ. No. WO 94/01778; and U.S. Pat. No. 6,150,087, the disclosures of which are incorporated herein by reference in their entireties.

Further, multiple epitope fusion antigens (termed "MEFAs"), as described in International Publ. No. WO 97/44469, may be used in the subject compositions. Such MEFAs include multiple epitopes derived from two or more of the various viral regions. The epitopes are preferably from more than one HCV strain, thus providing the added ability to protect against multiple strains of HCV in a single vaccine.

It should be noted that for convenience, the various HCV regions are generally defined with respect to the amino acid number relative to the polyprotein encoded by the genome of HCV-1a, as described in Choo et al. (1991) Proc Natl Acad Sci USA 88:2451, with the initiator methionine being designated position 1. However, the polypeptides for use with the present invention are not limited to those derived from the HCV-1a sequence. Any strain or isolate of HCV can serve as the basis for providing antigenic sequences for use with the invention. In this regard, the corresponding regions in another HCV isolate can be readily determined by aligning sequences from the two isolates in a manner that brings the sequences into maximum alignment.

Various strains and isolates of HCV are known in the art, which differ from one another by changes in nucleotide and amino acid sequence. For example, isolate HCV J1.1 is described in Kubo et al (1989) Japan. Nucl. Acids Res. 17:10367-10372; Takeuchi et al.(1990) Gene 91:287-291; Takeuchi et al. (1990) J. Gen. Virol. 71:3027-3033; and Takeuchi et al. (1990) Nucl. Acids Res. 18:4626. The complete coding sequences of two independent isolates, HCV-J and BK, are described by Kato et al., (1990) Proc. Natl. Acad. Sci. USA 87:9524-9528 and Takamizawa et al., (1991) J. Virol. 65:1105-1113, respectively. HCV-1 isolates are described by Choo et al. (1990) Brit. Med. Bull. 46:423-441; Choo et al. (1991) Proc. Natl. Acad. Sci. USA 88:2451-2455 and Han et al. (1991) Proc. Natl. Acad. Sci. USA 88:1711-1715. HCV isolates HC-J1 and HC-J4 are described in Okamoto et al. (1991) Japan J. Exp. Med. 60:167-177. HCV isolates HCT 18.about., HCT 23, Th, HCT 27, EC1 and EC10 are described in Weiner et al. (1991) Virol. 180:842-848. HCV isolates Pt-1, HCV-K1 and HCV-K2 are described in Enomoto et al. (1990) Biochem. Biophys. Res. Commun. 170:1021-1025. HCV isolates A, C, D & E are described in Tsukiyama-Kohara et al. (1991) Virus Genes 5:243-254. HCV polypeptides for use in the compositions and methods of the invention can be obtained from any of the above cited strains of HCV or from newly discovered isolates isolated from tissues or fluids of infected patients.

Other antigens useful in the present invention are those derived from HIV. The HIV genome includes the regions known as Gag (p55gag), Pol, Vif, Vpr, Tat, Rev, Vpu, Env and/or Nef. HIV antigens from any of these regions, from any of the various subtypes, such as HIV subtype B and HIV subtype C, as well as any of the various isolates will find use with the present methods. It will be readily apparent to one of ordinary skill in the art in view of the teachings of the present disclosure how to determine corresponding regions in other HIV strains or variants (e.g., isolates $HIV_{IIIb}$, $HIV_{SF2}$, $HIV-1_{SF162}$, $HIV-1_{SF170}$, $HIV_{LAV}$, $HIV_{LAI}$, $HIV_{MN}$, $HIV-1_{CM235}$, $HIV-1_{US4}$, other HIV-1 strains from diverse subtypes (e.g., subtypes, A through G, and 0), HIV-2 strains and diverse subtypes, and simian immunodeficiency virus (SIV). (See, e.g., Virology, 3rd Edition (W. K. Joklik ed. 1988); Fundamental Virology, 2nd Edition (B. N. Fields and D. M. Knipe, eds. 1991); Virology, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify the various regions).

The envelope protein of HIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells. The gp120 polypeptide is instrumental in mediating entry into the host cell. Recent studies have indicated that binding of CD4 to gp120 induces a conformational change in Env that allows for binding to a co-receptor (e.g, a chemokine receptor) and subsequent entry of the virus into the cell. (Wyatt, R., et al. (1998) Nature 393:705-711; Kwong, P., et al.(1998) Nature 393:648-659). CD4 is bound into a depression formed at the interface of the outer domain, the inner domain and the bridging sheet of gp120.

Recombinant methods of obtaining the various HIV antigens once the region desired is identified are well known in the art and are described further below. See, also, U.S. Pat. No. 5,614,612, incorporated herein by reference in its entirety.

Moreover, modified sequences of any of these HIV regions, such as modified gp120 and p55gag, can be used in the subject methods. Sequences can be modified for optimum codon usage to simulate human codons and to reduce toxicity. Such modified sequences are known in the art and the sequences and methods of producing the same are described in detail in commonly owned International Publication Nos. WO 00/39304 and WO 00/39302, as well as in International Publication No. WO 98/34640, all incorporated herein by reference in their entireties.

The subject methods are also useful for antigens derived from *Neisseria* spp., such as *N. meningitidis*, the causative agent of bacterial meningitis and sepsis. Meningococci are divided into serological groups based on the immunological characteristics of capsular and cell wall antigens. Currently recognized serogroups include A, B, C, W-135, X, Y, Z and 29E. For purposes of the present invention, a meningococcal antigen may be derived from any of the various known serogroups. The polysaccharides responsible for the serogroup specificity have been purified from several of these groups, including A, B, C, W-135 and Y. Effective capsular polysaccharide-based vaccines have been developed against meningococcal disease caused by serogroups A, C, Y and W135 and any of these vaccine antigens will find use in the present compositions and methods. See, e.g., International Publication Nos. WO 96/29412, WO 96/14086, WO 99/57280, WO 00/22430, WO 99/24578, WO 99/36544, as well as Tettelin et al. (2000) Science 287:1809-1815 and Pizza et al. (2000)

Science 287:1816-1820, all incorporated by reference herein in their entireties, for a description of various meningococcal protein antigens that will find use herein. Additionally, saccharide antigens, such as those from *N. meningitidis* serogroup A, C W135 and/or Y, such as described in Costantino et al. (1992) Vaccine 10:691-698 and Costantino et al. (1999) Vaccine 17:1251-1263 will find use herein. Other useful *Neisseria* antigens include those derived from *N. gonorrhorea*, for example, those described in International Publication Nos. WO 99/57280, WO 99/24578 and WO 99/36544.

For example, *N. meningitidis* serogroup B (termed "MenB" herein) accounts for a large percentage of bacterial meningitis in infants and children residing in the U.S. and Europe. Accordingly, antigens derived from MenB are particularly useful with the present compositions and methods, such as any of the antigens expressed by the various open reading frames (ORFs) of the MenB genome. See, e.g., International Publication No. WO 99/57280. Examples of such antigens include MenB proteins 961 and 287. Other meningococcal antigens for use herein include derivatives of the capsular MenB polysaccharide (termed "MenB PS derivatives" herein). Examples of MenB PS derivatives are described in EP Publication No. 504,202 B and U.S. Pat. No. 4,727,136. Also useful are molecular mimetics of unique epitopes of MenB PS as described in U.S. Pat. No. 6,030,619. Additionally, outer membrane vesicle preparations from MenB, such as those described in International Patent Application PCT/IB01/00166, Bjune et al. (1991) Lancet 338: 1093-1096, Fukasawa et al. (1999) Vaccine 17:2951-2958 and Rosenquist et al. (1998) Dev. Biol. Stand. 92:323-333. All of the above references are incorporated herein by reference in their entireties.

The complete genomic sequence of MenB, strain MC58, has been described. Tettelin et al., Science (2000) 287:1809. Several proteins that elicited serum bactericidal antibody responses have been identified by whole genome sequencing. Many of these proteins have sequences that are highly conserved among *Neisseria meningitidis*. Pizza et al., Science (2000) 287:1816. Accordingly, such antigens will find use in the present invention.

In some embodiments, proteins from which the protein particles are formed or the nucleic acids that encode the proteins from which nucleic acid particles are formed include, without limitation, viral proteins, fungal proteins, bacterial proteins, avian proteins, mammalian proteins and eukaryotic proteins, such as but not limited to albumin, gelatin, zein, casein, collagen and fibrinogen. In some embodiments, proteins from which the protein particles are formed include or the nucleic acids that encode the proteins from which nucleic acid particles are formed include, without limitation, proteins from the herpes virus family, including proteins derived from herpes simplex virus (HSV) types 1 and 2, such as HSV-1 and HSV-2 glycoproteins gB, gD and gH; proteins derived from cytomegalovirus (CMV) including CMV gB and gH; proteins derived from hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV); proteins, including gp120, gp160, gp41, p24gag and p55gag envelope proteins, derived from HIV such as, including members of the various genetic subtypes of HIV isolates $HIV_{IIIb}$, $HIV_{SF2}$, $HIV_{LAV}$, $HIV_{LAI}$, $HIV_{MN}$, $HIV-1_{CM235}$, $HIV-1_{US4}$, HIV-2; proteins derived from simian immunodeficiency virus (SIV); proteins derived from *Neisseria meningitidis* (A, B, C, Y), *Hemophilus influenza* type B (HIB), *Helicobacter pylori*; human serum albumin and ovalbumin.

Methods for producing particular protein particles are known in the art and discussed more fully below. Furthermore, for purposes of the present invention, "antigen" refers to polynucleotides and proteins which include modifications, such as deletions, additions and substitutions (generally conservative in nature), to the native sequence, so long as the protein maintains the ability to elicit an immunological response, as defined herein. These modifications may be deliberate, as through site-directed mutagenesis, or may be accidental, such as through mutations of hosts which produce the antigens.

Several detection techniques may be used in order to confirm that proteins have taken on the conformation of protein particles. Such techniques include electron microscopy, X-ray crystallography, and the like. See, e.g., Baker et al., Biophys. J. (1991) 60:1445-1456; Hagensee et al., J. Virol. (1994) 68:4503-4505. For example, cryoelectron microscopy can be performed on vitrified aqueous samples of the protein particle preparation in question, and images recorded under appropriate exposure conditions.

An antigen particle is "distinct from" a second antigen when the second antigen is not entrapped within the particles and/or the second antigen and particles are not expressed together as a fusion compound. However, an antigen particle is considered "distinct from" a selected second antigen even if there is a loose physical association between the second antigen and particle so long as the second antigen is not covalently bound to, entrapped within or adsorbed to the surface of the particle. In some embodiments, the first or second antigen is a protein or a nucleic acid molecule.

As used herein, the term "lysate" an extract or lysate derived from a cell which includes one or more antigens. By way of example, an "*H. pylori* lysate" refers to an extract or lysate derived from an *H. pylori* Type I or Type II whole bacterium which includes one or more *H. pylori* antigens. Thus, the term denotes crude extracts that contain several antigens, as well as relatively purified compositions derived from such crude lysates which include only one or few such antigens. Such lysates are prepared using techniques well known in the art.

Representative antigens that may be present in such lysates, either alone or in combination, include one or more antigens derived from the *H. pylori* adhesins such as, but not limited to, a 20 kDa α-acetyl-neuraminillactose-binding fibrillar haemagglutinin (HpaA), a 63 kDa protein that binds phosphatidyl-ethanolamine and gangliotetraosyl ceramide, and a conserved fimbrial pilus-like structure. See, e.g., Telford et al., Trends in Biotech. (1994) 12:420-426 for a description of these antigens. Other antigens that may be present in the lysate include epitopes derived from any of the various flagellins such as the major flagellin, FlaA and the minor flagellin, FlaB. In this regard, the flagella of *H. pylori* are composed of FlaA and FlaB, each with a molecular weight of approximately 53 kDa. Another representative antigen includes *H. pylori* urease which is associated with the outer membrane and the periplasmic space of the bacterium. The holoenzyme is a large complex made up of two subunits of 26.5 kDa (UreA) and 61 kDa (UreB), respectively. Epitopes derived from the holoenzyme, either of the subunits, or a combination of the three, can be present and are captured under the definition of "urease" herein. Another representative antigen that may be present in the lysate or used in further purified form includes the *H. pylori* heat shock protein known as "hsp60." The DNA and corresponding amino acid sequences for hsp60 are known. See, e.g., International Publication No. WO 93/18150, published Sep. 16, 1993. The full-length hsp60 antigen shown has about 546 amino acids and a molecular weight of about 58 kDa. The VacA and CagA antigens may also be present in such lysates. It is to be understood that the lysate can also include other antigens not specifically described herein.

By "VacA antigen" is meant an antigen as defined above which is derived from the antigen known as the *H. pylori* Type I Cytotoxin. The VacA protein induces vacuolization in epithelial cells in tissue culture and causes extensive tissue damage and ulceration when administered orally to mice. The DNA and corresponding amino acid sequences for VacA are known and reported in, e.g., International Publication No. WO 93/18150, published Sep. 16, 1993. The gene for the VacA antigen encodes a precursor of about 140 kDa that is processed to an active molecule of about 90-100 kDa. This molecule, in turn, is proteolytically cleaved to generate two fragments that copurify with the intact 90 kDa molecule. See, Telford et al., Trends in Biotech. (1994) 12:420-426. Thus, the definition of "VacA antigen" as used herein includes the precursor protein, as well as the processed active molecule, proteolytic fragments thereof or portions or muteins thereof, which retain specific reactivity with antibodies present in a biological sample from an individual with *H. pylori* Type I infection.

By "CagA antigen" is meant an antigen, as defined above, which is derived from the *H. pylori* Type I cytotoxin associated immunodominant antigen. CagA is expressed on the bacterial surface. The DNA and corresponding amino acid sequences for CagA are known. See, e.g., International Publication No. WO 93/18150, published Sep. 16, 1993. The full-length CagA antigen described therein includes about 1147 amino acids with a predicted molecular weight of about 128 kDa. The native protein shows interstrain size variability due to the presence of a variable number of repeats of a 102 bp DNA segment that encodes repeats of a proline-rich amino acid sequence. See, Covacci et al., Proc. Natl. Acad. Sci. USA (1993) 90:5791-5795. Accordingly, the reported molecular weight of CagA ranges from about 120-135 kDa. Therefore, the definition of "CagA antigen" as used herein includes any of the various CagA variants, fragments thereof and muteins thereof, which retain the ability to react with antibodies in a biological sample from an individual with *H. pylori* Type I infection. For example, the CagA polypeptide depicted in FIG. 3 of Covacci et al. is a truncated protein of 268 amino acids and includes Glu-748 to Glu-1015, inclusive, of the full-length molecule. Further, the definition of "CagA antigen" as used herein includes Nap protein of *H. pylori* antigen. See, e.g. PCT IB99/00695 for a description of Nap protein of *H. pylori* and methods to purify the same.

An immunogenic composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., J. Immunol. (1993) 151:4189-4199; Doe et al., Eur. J. Immunol. (1994) 24:2369-2376.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by, e.g., but not limited to B-cells; and/or the activation of suppressor T-cells and/or $\gamma\Delta$ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An immunogenic or vaccine composition which contains an antigen of the present invention, or an immunogenic or vaccine composition comprising an adjuvant and/or a second antigen which is coadministered with the subject antigen, displays "enhanced immunogenicity" when it possesses a greater capacity to elicit an immune response than the immune response elicited by an equivalent amount of the antigen administered using a different delivery system, e.g., wherein the antigen is administered as a soluble protein. Thus, an immunogenic or vaccine composition may display "enhanced immunogenicity" because the antigen is more strongly immunogenic or because a lower dose or fewer doses of antigen are necessary to achieve an immune response in the subject to which the antigen is administered. Such enhanced immunogenicity can be determined by administering the antigen composition and antigen controls to animals and comparing antibody titers and/or cellular-mediated immunity against the two using standard assays described herein.

Combinations of antigens derived from the one or more organisms can be conveniently used to elicit immunity to multiple pathogens in a single vaccine. An example of antigens in a multiple pathogen vaccine is a combination of bacterial surface oligosaccharides derived from MenC and Hib, conjugated to a nontoxic mutant carrier derived from a bacterial toxin, such as a nontoxic mutant of diphtheria toxin known as $CRM_{197}$. This conjugate is useful for preventing bacterial meningitis and is described in International Publication No. WO 96/14086, published May 17, 1996.

Methods and suitable conditions for forming particles from a wide variety of proteins are known in the art. For example, in the suspension cross-linking process, a solution of a protein is added to an immiscible liquid or an oil phase. The protein is dissolved in an appropriate solvent, such as an alcohol (methanol, ethanol, isopropanol, and the like), a ketone (methyl ethyl ketone, acetone, and the like), a glycol (ethylene glycol, propylene glycol, and the like) or an amide solvent (e.g., acetamide), containing between about 5% to about 90% of water. A precipitation agent is added to the protein solution form a protein particle. Oils such as mineral oil, silicone oil, or vegetable oil; hydrocarbons, such as hexane, heptane, dodecane, and high boiling petroleum ether; and coacervation agents such as acetone, ethanol, isopropanol, and the like, are useful as precipitation agents. The protein particles are dispersed by high-speed stirring, and stabilized using stabilization treatment, such as heat treatment or by treatment with a chemical cross-linking agent. In particular, stabilization is achieved by heating of the suspension to a temperature about 30° C. to about 150° C., preferably of about 35° C. to about 120° C., more preferably of about 40° C. to about 100° C. Alternatively the protein particles are stabilized by treatment with a chemical cross-linking agent, such as gluteraldehyde, butadione, and the like. See, e.g. WO 96/10992; Polymers in Controlled Drug Delivery, Eds. Illum, L. and Davis, S. S. (Wright, 1987) Chapter 3, pg 25; Torrado, J. J. et al., International Journal of Pharmaceutics, (1989) 51:85-93; Chen, G. Q. et al., Journal of Microencapsulation, (1994) 11(4):395-407.

In some embodiments, an aqueous solution of a protein, comprising about 0.1 to about 20% protein solution, about 0.5 to about 10%, and preferably about 1 to about 5% protein solution, is treated with an acid, until the pH is about 1 to about 6, about 1.5 to about 5, and preferably about 2 to about 4, wherein the acid includes, but is not limited to, acetic acid, glycolic acid, hydroxybutyric acid, hydrochloric acid, lactic acid, and the like. The solution is stirred at high speed, about 1,000 to about 25,000 rpm, about 2,000 to about 15,000, and preferably about 5,000 to about 10,000 rpm for about 1 minute to about 60 minutes, about 5 to about 45 minutes, and preferably about 10 to about 30 minutes. A coacervation agent is added to the stirring solution to form the protein particles, and the mixture is stirred for about 1 minute to about 60 minutes, about 5 to about 45 minutes, and preferably about 10 to about 30 minutes. Coacervation agents include, but are not limited to acetone, ethanol, isopropanol, and the like. The coacervation agent is optionally evaporated and the protein particles are stabilized by heating the mixture at about 30 to about 70° C., about 35 to about 65° C., and preferably about 40 to about 60° C., for about 1 minute to about 60 minutes, about 5 to about 45 minutes, and preferably about 10 to about 30 minutes, with stirring at about 1,000 to about 25,000 rpm, about 2,000 to about 15,000, and preferably about 5,000 to about 10,000 rpm. The protein particles may be sized, for example, in a Malvern Master sizer.

In some embodiments, an aqueous solution of the antigen, as described above, is added to a precipitation agent, such as mineral oil, silicone oil, or vegetable oil, and/or hydrocarbons, such as hexane, heptane, dodecane, and high boiling petroleum ether. The emulsion is stirred at high speed, about 1,000 to about 25,000 rpm, about 2,000 to about 15,000, and preferably about 5,000 to about 10,000 rpm for about 1 minute to about 60 minutes, about 5 to about 45 minutes, and preferably about 10 to about 30 minutes. The mixture is heated at about 30 to about 70° C., about 35 to about 65° C., and preferably about 40 to about 60° C., for about 1 minute to about 60 minutes, about 5 to about 45 minutes, and preferably about 10 to about 30 minutes, with stirring at about 1,000 to about 25,000 rpm, about 2,000 to about 15,000, and preferably about 5,000 to about 10,000 rpm to stabilize the antigen particles. The mixture is centrifuged and the antigen particles are collected. The antigen particles may be sized, for example, in a Malvern Master sizer.

Once obtained, antigen particles can be incorporated into immunogenic or vaccine compositions optionally comprising an adjuvant and/or a selected second antigen. The adjuvant and/or the second antigen can be administered separately, either simultaneously with, prior to, or subsequent to, the administration of the antigen particle composition. The compositions can be used both for treatment and/or prevention of infection. Furthermore, the formulations of the invention comprising protein particles may be used to enhance the activity of selected second antigens produced in vivo, i.e., in conjunction with DNA immunization.

Antigen particles can be used in compositions for immunizing a vertebrate subject against one or more pathogens or against subunit antigens derived from pathogens, or for priming an immune response to one or several antigens. Antigens that can be administered as a second antigen with the antigen particle include proteins, polypeptides, antigenic protein fragments, oligosaccharides, polysaccharides, and the like.

Similarly, an oligonucleotide or polynucleotide, encoding a desired antigen, can be administered with the antigen particle for in vivo expression.

As explained above, antigen particle formulations may or may not contain a second antigen of interest. For example, antigen particles may be formed from a combination of an appropriate nucleic acid molecule or protein and an antigen, or the antigens can be administered separately from the protein particle compositions at the same or at different sites. In any event, one or more selected antigens will be administered in a "therapeutically effective amount" such that an immune response can be generated in the individual to which it is administered. The exact amount necessary will vary depending on the subject being treated; the age and general condition of the subject to be treated; the capacity of the subject's immune system to synthesize antibodies and/or mount a cell-mediated immune response; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. In general, a "therapeutically effective" amount of antigen will be an amount on the order of about 0.1 µg to about 1000 µg, preferably about 1 µg to about 100 µg.

Similarly, antigens will be present in an amount such that a second antigen, if present, displays "enhanced immunogenicity," as defined above. Amounts which are effective for eliciting an enhanced immune response can be readily determined by one of skill in the art.

In some embodiments each adjuvant is present in the amount of about 0.06% to about 1% w/v, from about 0.1% to about 0.6% w/v, or 0.01% to about 2% w/v.

The compositions may additionally contain one or more "pharmaceutically acceptable excipients or vehicles" such as water, saline, glycerol, ethanol, etc. Additionally, auxiliary substances, such as wetting or emulsifying agents, biological buffers, and the like, may be present in such vehicles. A biological buffer can be virtually any solution which is pharmacologically acceptable and which provides the adjuvant formulation with the desired pH, i.e., a pH in the physiological range. Examples of buffer solutions include saline, phosphate buffered saline, Tris buffered saline (TBS), Hank's buffered saline (HBS), growth media such as Eagle's Minimum Essential Medium ("MEM"), and the like.

The second antigen is optionally associated with a carrier (e.g., the antigen may be encapsulated within, adsorbed on to, co-lyophilized or mixed with the carrier), wherein the carrier is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), polymeric particulate carriers, inactive virus particles and the like. Additionally, these carriers may function as additional immunostimulating agents. Furthermore, the antigen may be conjugated to a bacterial toxoid, such as toxoid from diphtheria, tetanus, cholera, etc. Examples of polymeric particulate carriers include particulate carriers formed from materials that are sterilizable, non-toxic and biodegradable. Such materials include, without limitation, poly(α-hydroxy acid), polyhydroxybutyric acid, polycaprolactone, polyorthoester and polyanhydride. Preferably, microparticles for use with the present invention are derived from a poly(a-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered second antigen (for a further discussion of particulate carriers for use herein, see commonly owned, U.S. patent application Ser. No. 09/124,533, filed on Jul. 29, 1998).

The adjuvant/second antigen may be conjugated on to the surface of the antigen using any of the several methods known in the art (see, e.g., Bioconjugate Techniques, Greg. T. Hermanson Ed., Academic Press, New York. 1996). For example, protein-protein (i.e. protein particle-second antigen) conjugation could be carried by using sulfo-SMCC linkers (sulfo-succinimidyl esters) for conjugation using standard protocols.

Adjuvants may also be used to enhance the effectiveness of the pharmaceutical compositions. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as, for example; (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.); (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and; (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see International Publication No. WO 99/30739, published Jun. 24, 1999); (3) saponin adjuvants, such as Stimulon™ (Cambridge Bioscience, Worcester, Mass.) may be used or particles generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, IL-3, IL-4, IL-S, IL-6, IL-7, IL-8, IL-9, IL-10, IL-11, IL-12, IL-13, IL-16, IL-17, IL-19, IL-20, and the like), macrophage colony stimulating factor (M-CSF), tumor necrosis factor (TNF), VEGF, CD27, CD30, CD40, Fas Ligand, Placenta Growth Factor, etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), adjuvants derived from the CpG family of molecules, CpG dinucleotides and synthetic oligonucleotides which comprise CpG motifs (see, e.g., Krieg et al., Nature, 374:546 (1995) and Davis et al., J. Immunol., 160:870-876 (1998)) and PT-K9/G129 (where lysine is substituted for the wild-type amino acid at position 9 and glycine substituted at position 129) (see, e.g., International Publication Nos. WO93/13202 and WO92/19265); (7) R-848 (see e.g., U.S. Pat. Nos. 5,352,784; 5,266,575; 4,929,624; 5,268,376; 5,389,640; 4,689,338; 5,482,936; 5,346,905; 5,395,937; 5,238,944; 5,252,612, and 6,110,929; and international publication WO99/29693); and (8) other substances that act as immunostimulating agents to enhance the effectiveness of the composition.

As used herein, the term "conventional adjuvants" refers to adjuvants that have been known and used previously in vaccine compositions, immunogenic compositions, or in compositions that have been used to generate an immune response. Examples of conventional adjuvants include, but are not limited to, aluminum salts (alum), oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™), saponin adjuvants, such as Stimulon™ or particle generated therefrom such as ISCOMs (immunostimulating complexes), Complete Freunds Adjuvant (CFA) and Incomplete Freunds Adjuvant (IFA), cytokines, such as interleukins (IL-1, IL-2, IL-3, IL-4, IL-5, IL-6, IL-7, IL-8, IL-9, IL-10, IL-11, IL-12, IL-13, IL-16, IL-17, IL-19, IL-20, and the like), macrophage colony stimulating factor (M-CSF), tumor necrosis factor (TNF), VEGF, CD27, CD30, CD40, Fas Ligand, Placenta Growth Factor, etc.; detoxified mutants of a bacterial ADP-ribosylating toxin such as a cholera toxin (CT), a pertussis toxin (PT), or an E. coli heat-labile toxin (LT), particularly LT-K63, LT-R72, CT-S109, adjuvants derived from the CpG family of molecules, CpG dinucleotides and synthetic oligonucleotides which comprise CpG motifs, and PT-K9/G129.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipahitoyl-sn-glycero-3-huydroxyphosphoryloxy)-ethylamine (MTP-PE), etc.

Once formulated, the compositions of the invention can be administered parenterally, e.g., by injection. The compositions can be injected either subcutaneously, intraperitoneally, intravenously or intramuscularly. Other modes of administration include oral and pulmonary administration, suppositories, mucosal and transdermal applications. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

EXAMPLES

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Preparation of Small Ovalbumin (OVA) Protein Particles

Ovalbumin (OVA, 200 mg) was dissolved in distilled water (10 ml) to form a 2% protein solution. Lactic acid (100 μl) was added to the OVA-solution until the pH was reduced to about 4.5-5.0. The solution was stirred over a magnetic stirrer at 1500 rpm for 10 minutes. Acetone (25 ml) was added to the stirring solution, and the mixture was left stirring for 10 minutes. The mixture was heated at 70° C. for 30 minutes with stirring at 5000 rpm to stabilize the protein particles. The protein particles were then sized in a Malvern Master sizer for future use (the protein particles were about 250 nm in diameter).

Example 2

Preparation of Large Ovalbumin (OVA) Protein Particles

Ovalbumin (OVA, 200 mg) was dissolved in distilled water (10 ml) to form a 2% protein solution. Lactic acid (100 μl) was added to the OVA-solution until the pH was reduced to about 4.5-5.0. The solution was stirred over a magnetic stirrer at 500 rpm for 10 minutes. Acetone (25 ml) was added to the stirring solution, and the mixture was left stirring for 10 minutes. The mixture was heated at 70° C. and stirred at 500 rpm for 30 minutes to stabilize the protein particles. The protein particles were lyophilized and then sized in a Malvern Master sizer and stored in a dessicator for future use (the protein particles were about 2.5 μm in diameter).

Example 3

Preparation of Small gB2 Protein Particles

HSVgB2 antigen (4.2 mg) was dissolved in distilled water (2 ml), and the solution was stirred over a magnetic stirrer at 1500 rpm. Acetone (2.5 ml) was added to the stirring solution, and the mixture was left stirring for 20 minutes. The mixture was then heated at 70° C. and left stirring for 25 minutes to stabilize the protein particles. The mixture was centrifuged at 30,000×g and the protein particles were collected. The particles were lyophilized and then sized in a Malvern Master sizer for future use (the protein particles were about 350 nm in diameter).

Example 4

Preparation of Large gB2 Protein Particles

HSVgB2 antigen (4.2 mg) was dissolved in distilled water (2 ml), and the solution was stirred over a magnetic stirrer at 750 rpm. Acetone (2.5 ml) was added to the stirring solution, and the mixture was left stirring for 20 minutes. The mixture was then heated at 70° C. and left stirring for 25 minutes to stabilize the protein particles. The mixture was centrifuged at 30,000×g and the protein particles were collected. The protein particles were lyophilized and then sized in a Malvern Master sizer for future use (the protein particles were about 5 μm in diameter).

Example 5

Preparation of PLG Particles

PLG (poly(lactideco-glycolides)) particles were prepared using polyvinyl alcohol (PVA) as follows. Solutions used were:

(1) 66% RG 503 PLG (Boehringer Ingelheim) in dichloromethane ("polymer solution");

(2) 8% polyvinyl alcohol (PVA) (ICN) in water ("PVA solution")

PLG particles were prepared by combining 10 ml of polymer solution with 40 ml of the PVA solution and homogenizing for 3 minutes using an Omni benchtop homogenizer with a 10 mm probe at 10 K rpm. The emulsion was left stirring overnight for solvent evaporation. The formed PLG particles were washed with water by centrifugation 4 times, and lyophilized. The PLG particles were then sized in a Malvern Master sizer for future use.

Example 6

Preparation of PLG OVA-Entrapped Particle Using A Solvent Evaporation Technique

In a 15 ml glass test tube were placed 1 ml of 10 mg/m OVA and 20 ml of 5% w:w PLG (poly D,L-lactide-co-glycolide) in dichloromethane, 50:50 mol ratio lactide to glycolide, MW average=70-100 kDa, (Medisorb Technologies International). The solution was homogenized for 2 minutes at high rpm using a hand held homogenizer. The homogenate was added to 80 ml of 10% polyvinyl alcohol (PVA) (12-23 kDa) in a 100 ml glass beaker. This was homogenized for two minutes at a 10,000 rpm using a bench scale homogenizer equipped with a 20 mm diameter generator. The solution was stirred at room temperature at a moderate rate using a magnetic stir bar until the solvents were evaporated. PLG OVA-entrapped particles were resuspended in water and washed several times with water, using centrifugation to pellet the particles between washes. The particles were dried in the presence of desiccant (Dririte $CaSO_4$) under vacuum. Mean volume size was determined to be 0.9 μm by laser diffraction measurement. Protein content of the PLG OVA-entrapped particles was determined to be 0.8% w:w by amino acid compositional analysis.

Example 7

Immunogenicity of Ovalbumin (OVA) Particles

Ovalbumin, PLG/OVA-entrapped particles, small OVA-protein particles (250 nm) and large OVA-protein particles (2500 nm), produced as described above, were administered subcutaneously to mice (dose=10 μg). The animals were boosted at 14 and 28 days. Serum was collected two weeks following the last immunization and CTL activity assayed as described in Doe et al., Proc. Natl. Acad. Sci. (1996) 93:8578-8583.

Lymphocyte cultures were prepared as follows. Spleen cells (sc) from immunized mice were cultured in 24-well dishes at $5 \times 10^6$ cells per well. Of those cells, $1 \times 10^6$ were sensitized with synthetic epitopic peptides from EG7 (EL4 transfected with ovalbumin) and EL4 proteins at a concentration of 10 μM for 1 hour at 37° C., washed, and cocultured with the remaining $4 \times 10^6$ untreated sc in 2 ml of culture medium [50% RPMI 1640 and 50% alpha-MEM (GIBCO)] supplemented with heat-inactivated fetal serum, $5 \times 10^{-5}$ M 2-mercaptoethanol, antibiotics, and 5% interleukin-2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. EG7 (EL4 transfected with ovalbumin) and EL4 target cells used in the $^{51}$Cr release assays express class I but not class II MHC molecules. Approximately $1 \times 10^6$ target cells were incubated in 200 μl of medium containing 50 μCi (1 Ci=37 Gbq) of $^{51}$Cr and synthetic Ovalbumin peptides (1 μm) for 60 min and washed three times. Effector (E) cells were cultured with $5 \times 10^3$ target (T) cells at various E/T ratios in 200 μl of culture medium in 96-well round-bottom tissue culture plates for 4 hours. The average cpm from duplicate wells was used to calculate percent specific $^{51}$Cr release.

The small and large OVA-protein particles elicited a CTL response and the small OVA-protein particles had activity comparable to the large OVA-protein particles. Both types of OVA-protein particles were more active, e.g., elicited a greater immune response than the PLG/OVA-entrapped particles and ovalbumin alone formulations.

Example 8

Preparation of PLG gB2-Entrapped Particle Using a Solvent Evaporation Technique

In a 15 ml glass test tube was placed 0.5 ml 5 mg/ml gB2 and 5 ml 6% w:w PLG (poly D,L-lactide-co-glycolide) in dichloromethane, 50:50 mol ratio lactide to glycolide, MW average=70-100 kDa, (Medisorb Technologies International). The solution was homogenized for 2 minutes at high rpm using a hand held homogenizer. The homogenate was added to 20 ml 8% polyvinyl alcohol (PVA) (12-23 kDa) in a 100 ml glass beaker. The mixture was homogenized for two minutes at a 10,000 rpm using a bench scale homogenizer equipped with a 20 mm diameter generator, The solution was stirred at room temperature at a moderate rate using a magnetic stir bar until the solvents were evaporated. PLG gB2-entrapped particles were resuspended in water and washed several times with water, using centrifugation to pellet the particles between washes. The particles were dried in the presence of desiccant (Dririte CasO$_4$) under vacuum. Mean volume size was determined to be 0.9 μm by laser diffraction measurement. Protein content of the PLG gB2-entrapped particles was determined to be 0.5% w:w by amino acid compositional analysis.

Example 9

Immunogenicity of gB2 Particles

The gB2 protein particles, PLG gB2-entrapped particles, produced as described above, as well as gB2 alone, without associated protein particles (as a negative control) and vaccinia gag-pol controls (as a positive control) were administered subcutaneously to mice (dose=5 μg). The animals were boosted at 7 and 14 days. Serum was collected two weeks following the last immunization and CTL activity assayed as described in Doe et al., Proc. Natl. Acad. Sci. (1996) 93:8578-8583.

The lymphocyte cultures were prepared as follows. Spleen cells (sc) from immunized mice were cultured in 24-well dishes at $5 \times 10^6$ cells per well. Of those cells, $1 \times 10^6$ were sensitized with synthetic epitopic peptides from HIV-1$_{SF2}$ proteins at a concentration of 10 μM for 1 hour at 37° C., washed, and cocultured with the remaining $4 \times 10^6$ untreated sc in 2 ml of culture medium [50% RPMI 1640 and 50% alpha-MEM (GIBCO)] supplemented with heat-inactivated fetal calf serum, $5 \times 10^{-5}$ M 2-mercaptoethanol, antibiotics, and 5% interleukin 2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. SvBALB (H-2$^d$) (SvB) and MCS7 (H-2$^b$) target cells used in the $^{51}$Cr release assays express class I but not class II MHC molecules. Approximately $1 \times 10^6$ target cells were incubated in 200 μl of medium containing 50 μCi (1 Ci=37 Gbq) of $^{51}$Cr and synthetic HIV-1 peptides (1 mM) for 60 min and washed three times. Effector (E) cells were cultured with $5 \times 10^3$ target (T) cells at various E/T ratios in 200 μl of culture medium in 96-well round-bottom tissue culture plates for 4 hours. The average cpm from duplicate wells was used to calculate percent specific $^{51}$Cr release.

The gB2 protein particles were less active than the vaccinia control and were more active than the PLG/gBf2-entrapped particles and the gB2 protein formulation (data not shown).

Example 10

Preparation of Virus Envelope Protein (gp120) with an Adjuvant (R848) on Polymer Microparticles for Administration to Mice Microparticles were prepared by a solvent evaporation technique by homogenizing 10 ml of 6% w/v polymer solution in methylene chloride with 2.5 ml PBS using a 10-mm probe (Ultra-Turrax T25 IKA-Labortechnik, Germany) for 2 minutes, thus forming a water in oil emulsion. This emulsion was then added to 50 ml of distilled water containing 6 ug/ml DSS and homogenized at 15,000 rpm using a 20-mm probe (ES-15 Omni International, GA, USA) for 25 minutes in an ice bath, resulting in the formation of water in oil in water emulsion which was stirred at 1000 rpm for 12 hours at room temperature, and the methylene chloride was allowed to evaporate.

A suspension containing 100 mg of PLG was incubated with 1 mg gp120 protein and 1 mg R848 in 10 ml total volume PBS. The suspension was then agitated on a lab rocker (Aliquot Mixer, Miles Laboratories) at 4° C. overnight. The suspension was then aliquoted into small glass vials and lyophilized with manitol at 5.5% wt/v.

Lyophilized product was resuspended in water for injection by briefly vortexing and administered by intra-muscular injection into mice, with 50 µL given into each leg, resulting in a total of 100 µL containing 10 µg of the antigen env gp120, 1 mg of RG503(PLG), and the formulated adjuvants at the dosages described.

Figure 2:
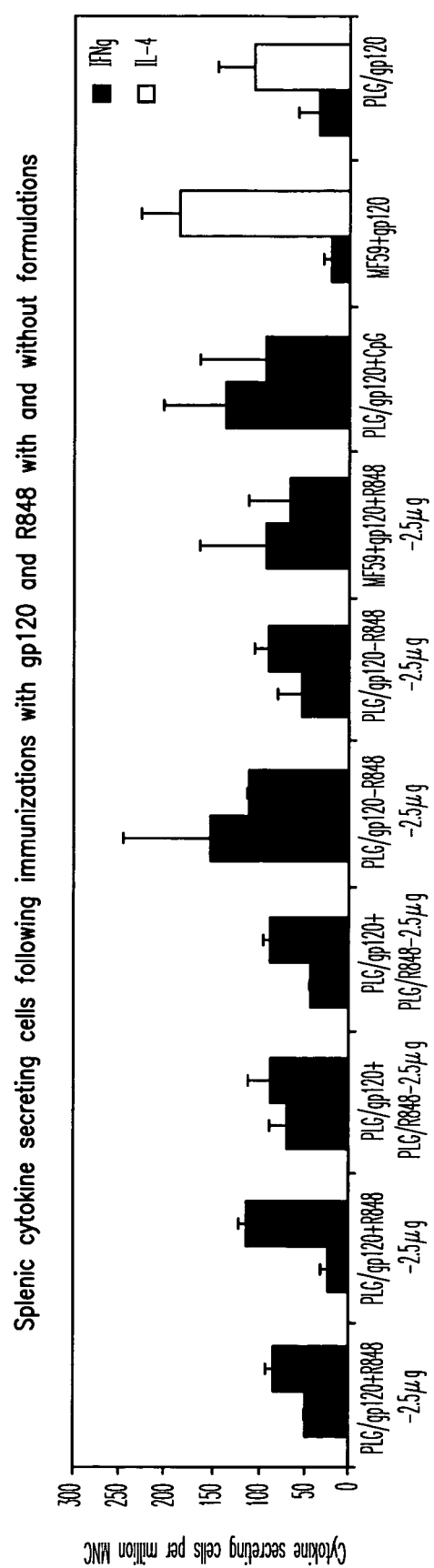
FIG. 2 shows levels of splenic cytokine secreting cells from mice immunized with gp120 associated with PLG plus R848 (2.5 µg); gp120 associated with PLG plus R848 (25 µg); gp120 associated with PLG plus R848 (2.5 µg) associated with PLG; gp120 associated with PLG plus R848 (25 µg) associated with PLG; gp120 associated with PLG and with R848 (2.5 µg); gp120 associated with PLG and with R848 (25 µg); gp120 and MF59 and R848 (25 µg); gp120 associated with PLG, plus CpG; gp120 plus MF59; and gp120 associated with PLG. Bars show the geometric mean cell number (GMT) of the group of mice. The error bars represent standard error of the mean.
Figure 3:
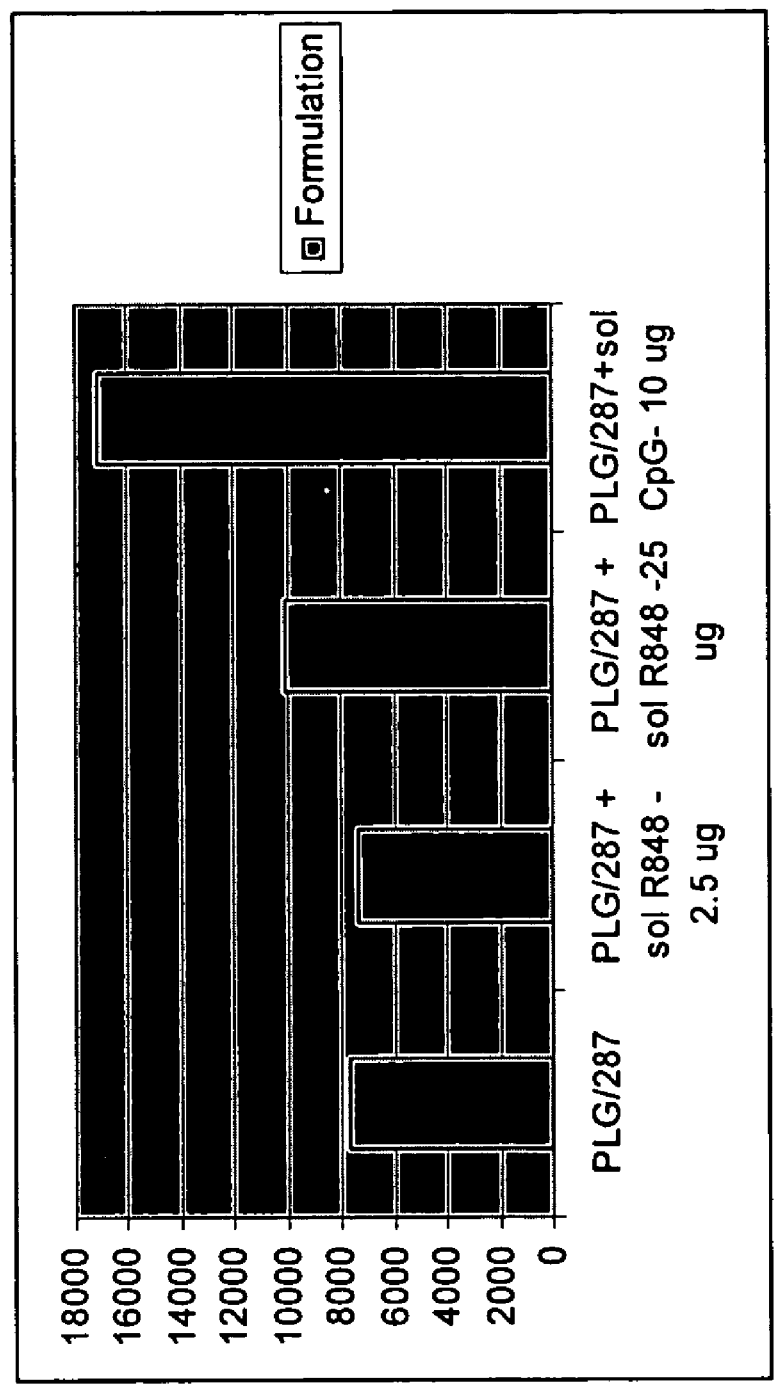
FIG. 3 shows antibody titers from mice immunized with: MenB Orf287 associated with PLG; MenB Orf287 associated with PLG plus soluble R848 (2.5 µg); MenB Orf287 associated with PLG plus soluble R848 (25 µg); MenB Orf287 associated with PLG plus soluble CpG (10 µg). Bars show the geometric mean antibody titer (GMT) of the group of mice. The error bars represent standard error of the mean.

FIGS. 1-2 demonstrate that the compositions of the present invention have an inhibitory effect on induction of antigen (Ag)-specific IFNγ-secreting cells, while having no inhibitory or stimulatory effect on the induction of antigen-specific IL4-secreting cells. Data is shown for antigens coadministered with R-848 and/or PLG's and/or MF59. Also shown are data with PLGs comprising the MenB ORF287 antigen with PLG and CpG (FIG. 3).

Thus, novel compositions and methods for using and making the same are disclosed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the subject matter described herein.

All publications, patents and patent applications cited herein, whether supra or infra, are hereby incorporated by reference in their entirety.

We claim:

1. An immunogenic composition comprising (a) a first antigen, (b) at least two adjuvants, wherein a first adjuvant comprises poly(lactide) polymer and/or poly(lactide-co-glycolide) polymer, wherein a second adjuvant comprises an imidazoquinoline, wherein said second adjuvant is co-lyophilized with said first adjuvant and wherein the first antigen is co-lyophilized with said first adjuvant, and (c) a pharmaceutically acceptable excipient, wherein said composition elicits a cellular immune response when administered to a vertebrate subject.

2. The immunogenic composition of claim 1 wherein said first antigen is in the form of a particle.

3. The immunogenic composition of claim 1 wherein said first antigen is a nucleic acid molecule.

4. The immunogenic composition of claim 3 wherein said nucleic acid molecule is DNA or RNA.

5. The immunogenic composition of claim 3 wherein said nucleic acid molecule is linked to a regulatory sequence which controls expression of said nucleic acid molecule.

6. The immunogenic composition of claim 1 wherein said first antigen is a protein.

7. The immunogenic composition of claim 1 further comprising at least a second pharmaceutically acceptable excipient.

8. The immunogenic composition of claim 6 wherein said protein is selected from the group consisting of a viral, fungal, bacterial, avian and mammalian protein.

9. The immunogenic composition of claim 8 wherein the viral protein is a herpes simplex virus type 2, hepatitis C virus (HCV), meningococcal antigen, or a human immunodeficiency virus (HIV) protein.

10. The immunogenic composition of claim 9 wherein said HCV protein is E1E2 polypeptide.

11. The immunogenic composition of claim 9 wherein said meningococcal antigen is a MenB protein from ORFs 287 and/or 961 of MenB.

12. The immunogenic composition of claim 8 wherein the protein is ovalbumin, HSVgB2, gp120, p55gag, or combinations thereof.

13. The immunogenic composition of claim 1 wherein at least one adjuvant is present in an amount from about 0.01% to about 2% w/v.

14. The immunogenic composition of claim 13 wherein at least one adjuvant is present in an amount from about 0.06% to about 1% w/v.

15. The immunogenic composition of claim 14 wherein at least one adjuvant is present an amount from about 0.1% to about 0.6% w/v.

16. The immunogenic composition of claim 1 wherein the composition comprises R-848.

17. The immunogenic composition of claim 1 comprising a further adjuvant comprising MF59.

18. The immunogenic composition of claim 16 comprising a further adjuvant.

19. The immunogenic composition of claim 1 comprising a further adjuvant.

20. The immunogenic composition of any one of claims 18 or 19 wherein the further adjuvant comprises aluminum salts, MF59, SAF, an adjuvant system comprising squalene and one or more bacterial cell wall components, saponin adjuvants, Complete Freunds Adjuvant (CFA), Incomplete Freunds Adjuvant (IFA), one or more cytokines, macrophage colony stimulating factor (M-CSF), tumor necrosis factor (TNF), VEGF, CD27, CD30, CD40, Fas Ligand, Placenta Growth Factor, detoxified mutants of a bacterial ADP-ribosylating toxin, CpG adjuvants, PT-K9/G129, or combinations thereof.

21. The immunogenic composition of claim 1 further comprising a second antigen distinct from the first antigen.

22. The immunogenic composition of claim 21 wherein the second antigen is a soluble or neutralizing antigen.

23. The immunogenic composition of claim 21 wherein said second antigen is a protein or a nucleic acid molecule.

24. The immunogenic composition of claim 21 wherein the second antigen is conjugated to an adjuvant.

25. The immunogenic composition of claim 21 wherein the second antigen is associated with a carrier.

26. The immunogenic composition of claim 24 wherein the carrier is a protein, polysaccharide, a polylactic acid, a polyglycolic acid, a polymeric amino acid, an amino acid copolymer, a lipid aggregate, a polymeric particulate carrier, or an inactive virus particle.

27. The immunogenic composition of claim 26 wherein the polymeric particulate carrier comprises a polymer selected from the group consisting of a poly(α-hydroxy acid), a polyhydroxy butyric acid, a polycaprolactone, a polyorthoester, and a polyanhydride.

28. The immunogenic composition of claim 1 wherein the first antigen is a stabilized antigen particle produced by a process comprising the steps of:
  (a) adding a precipitation agent to an aqueous solution of an antigen and stirring the resulting mixture to form an antigen particle;
  (b) stabilizing the antigen particle by a stabilizing treatment; and
  (c) recovering the stabilized antigen particle from the aqueous solution.

29. The immunogenic composition of claim 28 wherein said first antigen is a protein or a nucleic acid molecule.

30. The immunogenic composition of claim 28 wherein said imidazoquinoline is R-848.

31. The immunogenic composition of claim 28 wherein the immunogenic composition further comprises MF59.

32. The immunogenic composition of claim 28 further comprising a second pharmaceutically acceptable excipient.

33. The immunogenic composition of claim 28 wherein the aqueous solution in step (a) further comprises an acid.

34. The immunogenic composition of claim 28 wherein the process comprises a solvent evaporation technique.

35. The immunogenic composition of claim 33 wherein the acid is one or more of acetic acid, glycolic acid, hydroxybutyric acid, hydrochloric acid or lactic acid.

36. The immunogenic composition of claim 28 wherein the precipitation agent comprises one or more of oils, hydrocarbons or coacervation agents.

37. The immunogenic composition of claim 28 wherein the stabilizing treatment comprises one or more of heat treatment or treatment with a chemical cross-linking agent.

38. The immunogenic composition of claim 28 wherein the stabilized antigen particle elicits a cellular immune response in a vertebrate subject and is formed from a protein selected from the group consisting of a tumor, a viral, a fungal, a bacterial, an avian and a mammalian protein.

39. The immunogenic composition of claim 28 wherein the vertebrate subject is a human.

40. The immunogenic composition of claim 38 wherein the protein is a herpes simplex virus type 2 protein, hepatitis C virus (HCV) protein, an influenza A virus protein, or a human immunodeficiency virus (HIV) protein, or an immunogenic fragment of a herpes simplex virus type 2 protein, a hepatitis C virus (HCV) protein, an influenza A virus protein, or a human immunodeficiency virus (HIV) protein, or combinations thereof.

41. The immunogenic composition of claim 40 wherein the protein is E1E2 polypeptide, HSVgB2, gp120, p55gag, MenB protein from ORFs 287 and/or 961, immunogenic fragments of E1E2 polypeptide, HSVgB2 or gp120, p55gag, MenB protein from ORFs 287 and/or 961, or combinations thereof.

42. The immunogenic composition of claim 38 wherein the bacterial protein is pertussis protein, a diphtheria protein, a meningitis protein, a *H. pylori* protein, a *H. influenza* B protein, or a tetanus protein, immunogenic fragments of a pertussis protein, a diphtheria protein, a meningitis protein, a *H. pylori* protein, a *H. influenza* B protein, or a tetanus protein, or combinations thereof.

43. The immunogenic composition of claim 38 wherein the cellular immune response is a cytotoxic-T lymphocyte (CTL) response.

44. The immunogenic composition of claim 2 or claim 28 wherein the immunogenic composition further comprises a second antigen.

45. The immunogenic composition of any one of claims 9 or 40 wherein the HCV antigen is HCV core protein, E1, E2, NS3, NS4, or NS5, or an immunogenic fragment of HCV core protein, E1, E2, NS3, NS4, or NS5, or combinations thereof.

46. The immunogenic composition of any one of claims 9 or 40 wherein the HIV protein is gp120, gp160, gp41, p24gag or p55gag, or a fragment of gp120, gp160, gp41, p24gag or p55gag, or combinations thereof.

47. The immunogenic composition of claim 28 wherein the stabilized antigen particle is generally spherical.

48. The immunogenic composition of claim 28 wherein the stabilized antigen particle has a diameter from about 200 nanometers to about 10 microns.

49. The immunogenic composition of claim 28 wherein the stabilized antigen particle has a diameter ranging from about 500 nanometers to about 5 microns.

50. A method for eliciting a cytotoxic-T lymphocyte (CTL) response in a vertebrate subject comprising administering to the vertebrate subject an immunogenic composition of any one of claims 28 or 1.

51. The method of claim 50 wherein the vertebrate subject is a human.

52. The method of claim 50 wherein the immunogenic composition is co-administered to the subject prior or subsequent to, or concurrent with, a further adjuvant and/or a second antigen.

53. A method of eliciting an immune response in a vertebrate subject comprising administering to the vertebrate subject a effective amount of the immunogenic composition according to any one of claims 28 or 1.

54. The method of claim 52 wherein the vertebrate subject is a human.

55. The method of claim 50 wherein the immunogenic composition is administered by a route of intramuscular, intratracheal, intranasal, transdermal, intradermal, subcutaneous, intraocular, vaginal, rectal, intraperitoneal, intraintestinal or inhalation administration.

56. The method of claim 52 wherein the immunogenic composition is administered by a route of intramuscular, intratracheal, intranasal, transdermal, intradermal, subcutaneous, intraocular, vaginal, rectal, intraperitoneal, intraintestinal or inhalation administration.

57. The method of claim 50 wherein the immunogenic composition is delivered by a device selected from the group consisting of a particle accelerator, a pump, an intradermal applicator, a biolistic injector, a pneumatic injector, a sponge depot, a pill, and a tablet.

58. The method of claim 52 wherein the immunogenic composition is delivered by a device selected from the group consisting of a particle accelerator, a pump, an intradermal applicator, a biolistic injector, a pneumatic injector, a sponge depot, a pill, and a tablet.

59. The method of claim 50 wherein the immunogenic composition is delivered by needle-free injection.

60. The method of claim 52 wherein the immunogenic composition is delivered by needle-free injection.

61. An injectable vaccine composition comprising an immunogenic composition of any one of claims 28 or 1.

62. The injectable vaccine of claim 61 wherein the vaccine is administered by via intramuscular injection.

63. The injectable vaccine of claim 61 wherein the vaccine is administered via a needle-free injection device.

64. A method of eliciting an antibody-mediated immune response in an individual comprising administering the immunogenic composition of any one of claims 28 or 1 to said individual.

65. The immunogenic composition of claim 1 wherein the first antigen is is stabilized antigen particle produced by a process comprising:
   (a) combining a precipitation agent with an aqueous solution comprising an antigen;
   (b) dispersing the resultant mixture to form antigen particles;
   (c) stabilizing the dispersed antigen particles by a stabilizing treatment; and
   (d) recovering the stabilized antigen particles.

66. The immunogenic composition claim 65 wherein said antigen is a protein or a nucleic acid molecule.

67. The immunogenic composition of claim 65 wherein the process further comprises a solvent evaporation technique.

68. The immunogenic composition of claim 1, wherein the first antigen is a stabilized antigen particle capable of eliciting a cytotoxic-T lymphocyte (CTL) response, wherein the stabilized antigen particle is a generally spherical particle that is produced by a process comprising:
(a) forming an antigen particle from an antigen;
(b) stabilizing the antigen particle by a stabilizing treatment, wherein the stabilized antigen particle is not a virus-like particle, and wherein the stabilized antigen particle is not entrapped within a carrier.

69. The immunogenic composition of claim 68 wherein said antigen is a protein or a nucleic acid molecule.

70. The immunogenic composition of claim 68 wherein the process comprises a solvent evaporation technique.

71. The immunogenic composition of claim 68 wherein the stabilizing treatment is one or more of a heat treatment process or a chemical cross-linking process.

72. The immunogenic composition of claim 68 wherein the stabilized antigen particle is formed by a precipitation process.

73. The immunogenic composition of claim 72 wherein the precipitation process comprises combining an aqueous protein solution with one or more of an oil, a hydrocarbon or a coacervation agent.

74. The immunogenic composition of claim 72 wherein the stabilized antigen particle is formed by an emulsion process.

75. The immunogenic composition of claim 68 wherein the stabilized antigen particle is formed from a tumor protein antigen, a viral protein antigen, or a bacterial protein antigen.

76. The immunogenic composition of claim 75 wherein the viral protein is a herpes simplex virus type 2 protein, hepatitis C virus (HCV) protein, an influenza A virus protein, or a human immunodeficiency virus (HIV) protein, or an immunogenic fragment of a herpes simplex virus type 2 protein, a hepatitis C virus (HCV) protein, an influenza A virus protein, or a human immunodeficiency virus (HIV) protein, or combinations thereof.

77. The immunogenic composition of claim 75 wherein the bacterial protein is a pertussis protein, a diphtheria protein, a meningitis protein, a *H. pylori* protein, a *H. influenza* B protein, or a tetanus protein, or immunogenic fragments of a pertussis protein, a diphtheria protein, a meningitis protein, a *H. pylori* protein, a *H. influenza* B protein, or a tetanus protein, or combinations thereof.

78. The immunogenic composition of claim 76 wherein the protein is HSVgB2, gp120, HCV core protein, E1, E2, NS3, NS4, or NS5, or an immunogenic fragment of HCV core protein, E1, E2, NS3, NS4, NS5, HSVgB2 or gp120, or combinations thereof.

79. The immunogenic composition of claim 68 further comprising an additional antigen, wherein the additional antigen is distinct from the stabilized antigen particle.

80. The immunogenic composition of claim 68 wherein the stabilized antigen particle has a diameter from about 200 nanometers to about 10 microns.

81. The immunogenic composition of claim 68 wherein the stabilized antigen particle has a diameter from about 500 nanometers to about 5 microns.

82. A pharmaceutical composition comprising an immunogenic composition of any one of claims 28 or 1.

83. A kit for preparing an immunogenic composition of claim 1 comprising a first container comprising an antigen co-lyophilized with a poly(lactide) polymer and/or poly(lactide-co-glycolide) polymer, a second container comprising an imidazoquinoline co-lyophilized with a poly(lactide) polymer and/or poly(lactide-co-glycolide) polymer.

84. The kit of claim 83 wherein said imidazoquinoline comprises R-848.

85. The kit of claim 83 wherein the antigen is a tumor protein, a viral protein, a bacterial protein, a fungal protein, an avian protein, or a mammalian protein, or fragments of a viral protein, a bacterial protein, a fungal protein, an avian protein, or a mammalian protein.

86. The immunogenic composition of claim 1, wherein the first antigen and second adjuvant are together co-lyophilized with said first adjuvant.

87. The immunogenic composition of claim 1, wherein the first antigen and second adjuvant are independently co-lyophilized with said first adjuvant.

88. The immunogenic composition of claim 20, wherein the bacterial ADP-ribosylating toxin is a cholera toxin (CT), a pertussis toxin (PT), or an *E. coli* heat-labile toxin (LT).

89. The immunogenic composition of claim 1, wherein the antigen is human immunodeficiency virus (HIV) gp 120 protein and wherein the imidazoquinoline is R-848.

\* \* \* \* \*